(12) United States Patent
Argentine

(10) Patent No.: US 10,531,972 B2
(45) Date of Patent: *Jan. 14, 2020

(54) DELIVERY SYSTEM HAVING A SINGLE HANDED DEPLOYMENT HANDLE FOR A RETRACTABLE OUTER SHEATH

(71) Applicant: Medtronic Vascular, Inc., Santa Rosa, CA (US)

(72) Inventor: Jeffery Argentine, Petaluma, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 487 days.

This patent is subject to a terminal disclaimer.

(21) Appl. No.: 15/244,157

(22) Filed: Aug. 23, 2016

(65) Prior Publication Data

US 2017/0027725 A1  Feb. 2, 2017

Related U.S. Application Data

(63) Continuation of application No. 13/906,079, filed on May 30, 2013, now Pat. No. 9,445,928.

(51) Int. Cl.
*A61F 2/966* (2013.01)
*A61F 2/844* (2013.01)
*A61F 2/95* (2013.01)

(52) U.S. Cl.
CPC .............. *A61F 2/966* (2013.01); *A61F 2/844* (2013.01); *A61F 2002/9517* (2013.01)

(58) Field of Classification Search
CPC .......... A61M 25/0133; A61M 25/0136; A61M 25/0147; A61M 25/0169; A61M 25/0172; A61F 2002/9517; A61F 2002/011; A61F 2/96695; A61F 2/2427; A61F 2/2436; A61B 2017/00367
USPC .................. 606/1, 108; 623/1.11, 1.12, 2.11; 604/905.01, 95.04, 528
See application file for complete search history.

(56) References Cited

U.S. PATENT DOCUMENTS

| | | | |
|---|---|---|---|
| 2009/0018553 A1* | 1/2009 | McLean | A61B 17/0401 606/144 |
| 2010/0036472 A1* | 2/2010 | Papp | A61F 2/95 623/1.11 |
| 2010/0168756 A1 | 7/2010 | Dorn et al. | |
| 2010/0174290 A1* | 7/2010 | Wuebbeling | A61F 2/95 606/108 |
| 2011/0282425 A1 | 11/2011 | Dwork | |

(Continued)

*Primary Examiner* — Katherine M Shi
(74) *Attorney, Agent, or Firm* — Medler Ferro Woodhouse & Mills PLLC

(57) ABSTRACT

A delivery system for delivering a prosthesis, the delivery system including a housing, a sheath extending from within the housing, a clutching mechanism housed within the housing, and a cable. The clutching mechanism includes a one-way clutch that transmits a torque from an actuator to an inner shaft assembly when the actuator is rotated in a first direction and does not transmit a torque from the actuator to the inner shaft assembly when the actuator is rotated in a second opposing direction. The actuator is accessible from an exterior of the housing. The cable has a first end coupled to a proximal portion of the sheath and a second end coupled to the inner shaft assembly, and actuation of the actuator causes the actuator to rotate in the first direction, thereby causing the inner shaft assembly to wind up a portion of cable and retract the sheath.

20 Claims, 15 Drawing Sheets

(56) References Cited

U.S. PATENT DOCUMENTS

2012/0053574 A1    3/2012  Murray, III et al.
2012/0197303 A1*  8/2012  King ................. A61B 17/1728
                                                         606/282

* cited by examiner

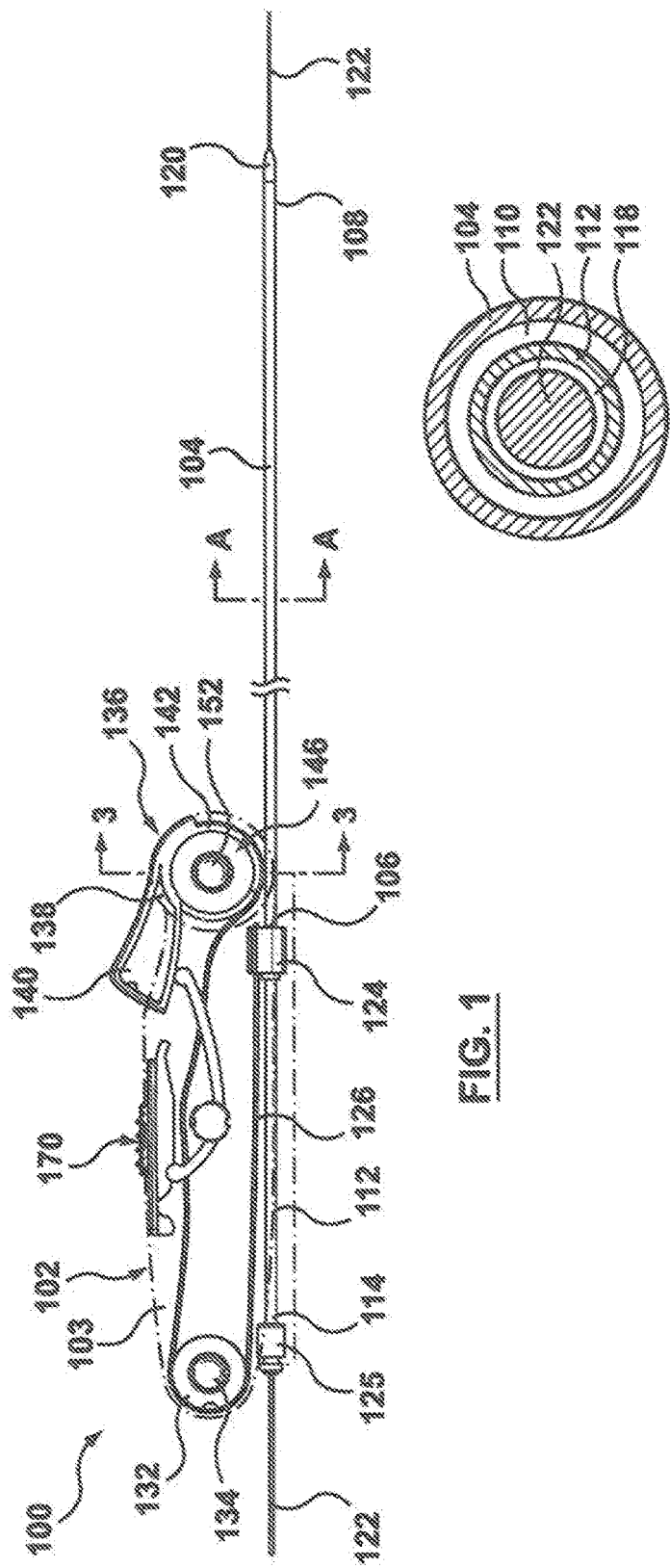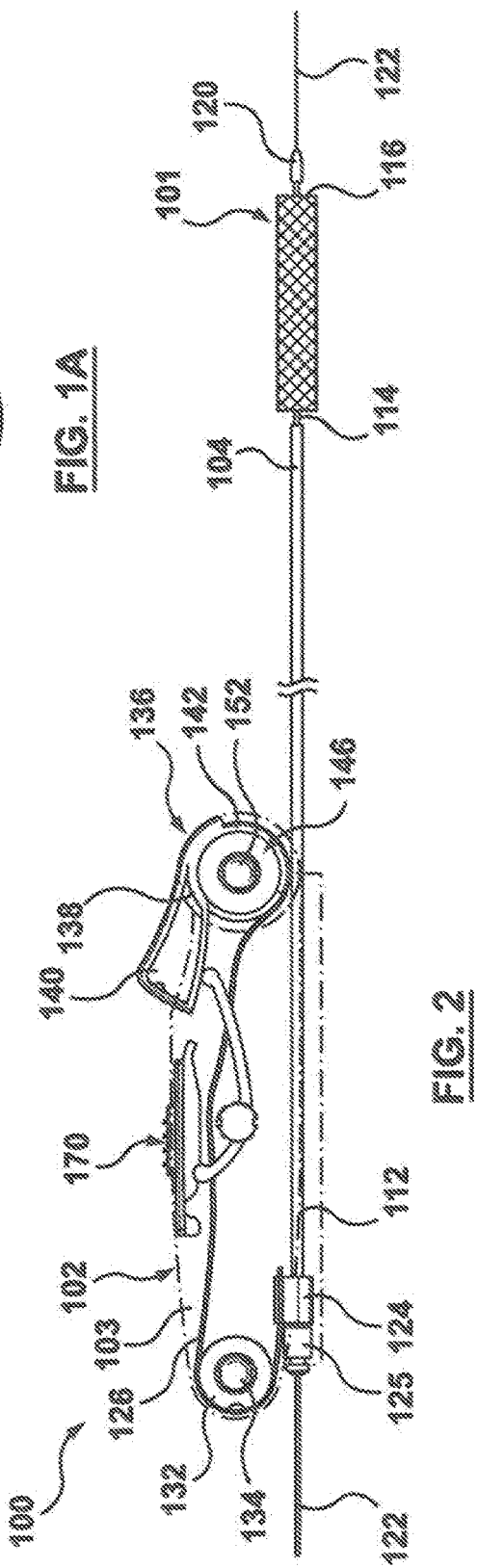

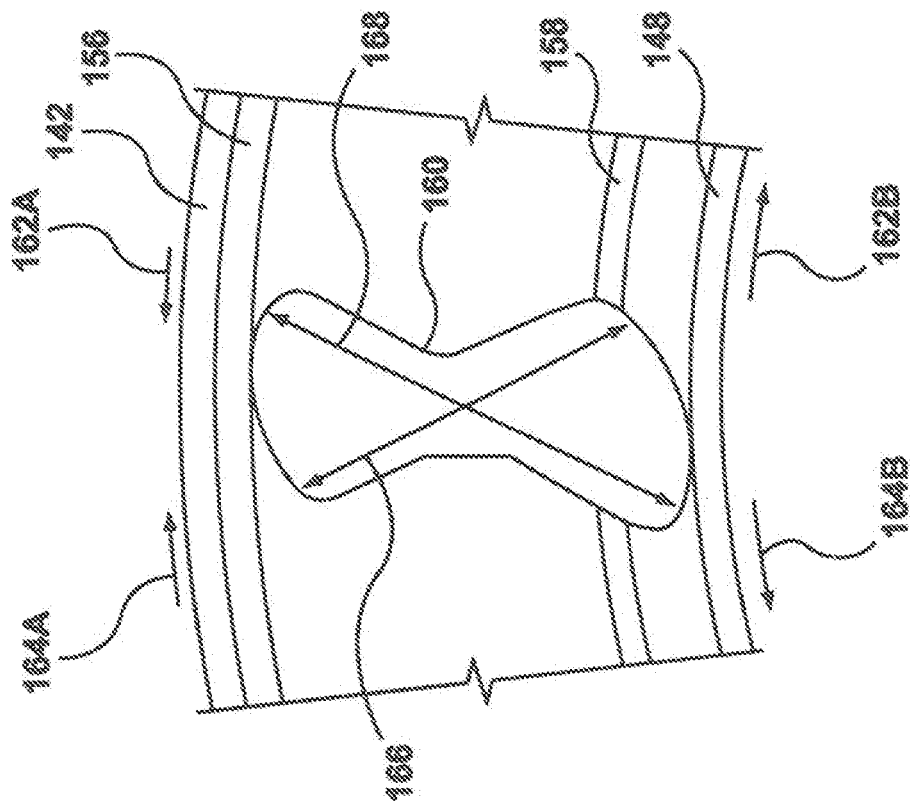
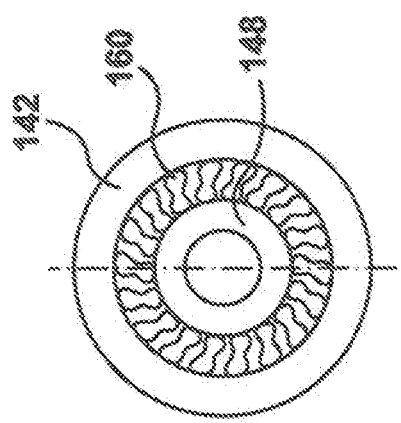

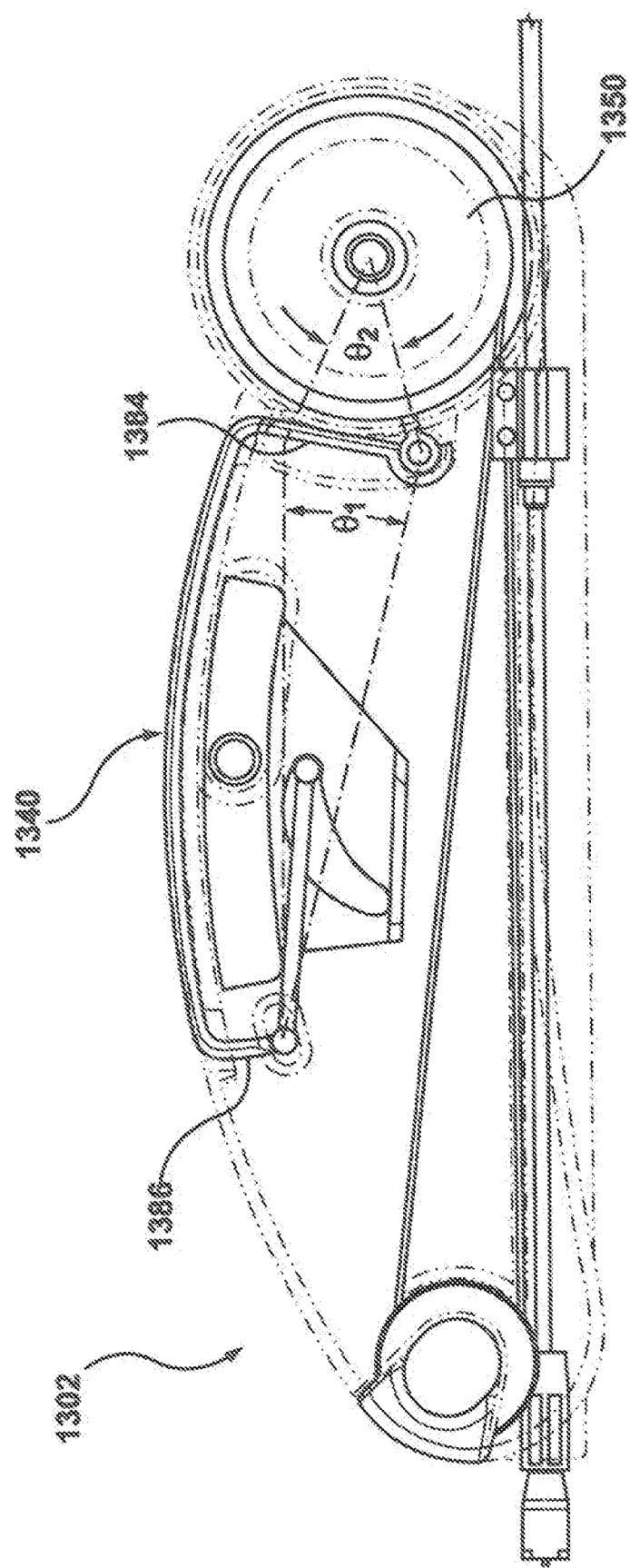

DELIVERY SYSTEM HAVING A SINGLE HANDED DEPLOYMENT HANDLE FOR A RETRACTABLE OUTER SHEATH

RELATED APPLICATIONS

This application is a Continuation of and claims the benefit of U.S. patent application Ser. No. 13/906,079, filed May 30, 2013, now allowed. The disclosures of which are herein incorporated by reference in their entirety.

FIELD OF THE INVENTION

Embodiments hereof relate to delivery systems and methods for deploying a prosthesis within a body lumen.

BACKGROUND OF THE INVENTION

Prostheses for implantation in blood vessels or other similar organs of the living body are, in general, well known in the medical art. For example, prosthetic vascular grafts constructed of biocompatible materials have been employed to replace or bypass damaged or occluded natural blood vessels. In general, endovascular grafts typically include a graft anchoring component that operates to hold a tubular graft component of a suitable biocompatible material in its intended position within the blood vessel. Most commonly, the graft anchoring component is one or more radially compressible stents that are radially expanded in situ to anchor the tubular graft component to the wall of a blood vessel or anatomical conduit. Thus, endovascular grafts are typically held in place by mechanical engagement and friction due to the opposition forces provided by the radially expandable stents.

Grafting procedures are also known for treating aneurysms. Aneurysms result from weak, thinned blood vessel walls that "balloon" or expand due to aging, disease and/or blood pressure in the vessel. Consequently, aneurysmal vessels have a potential to rupture, causing internal bleeding and potentially life threatening conditions. Grafts are often used to isolate aneurysms or other blood vessel abnormalities from normal blood pressure, reducing pressure on the weakened vessel wall and reducing the chance of vessel rupture. As such, a tubular endovascular graft may be placed within the aneurysmal blood vessel to create a new flow path and an artificial flow conduit through the aneurysm, thereby reducing if not nearly eliminating the exertion of blood pressure on the aneurysm.

In general, rather than performing an open surgical procedure to implant a bypass graft that may be traumatic and invasive, endovascular grafts which may be referred to as stent-grafts are preferably deployed through a less invasive intraluminal delivery procedure. More particularly, a lumen or vasculature is accessed percutaneously at a convenient and less traumatic entry point, and the stent-graft is routed through the vasculature to the site where the prosthesis is to be deployed. Intraluminal deployment is typically effected using a delivery catheter with coaxial inner and outer tubes arranged for relative axial movement. For example, a self-expanding stent-graft may be compressed and disposed within the distal end of the outer tube or sheath distal of a stop fixed to the inner tube. The catheter is then maneuvered, typically routed through a body lumen until the end of the catheter and the stent-graft are positioned at the intended treatment site. The stop on the inner tube is then held stationary while the outer sheath of the delivery catheter is withdrawn. The stop prevents the stent-graft from being withdrawn with the outer sheath. As the outer sheath is withdrawn, the stent-graft is released from the confines of the outer sheath and radially self-expands so that at least a portion of it contacts and substantially conforms to a portion of the surrounding interior of the lumen, e.g., the blood vessel wall or anatomical conduit wall.

A stent-graft may be tightly compressed within a catheter for delivery, imposing high levels of friction between the stent-graft and the outer sheath of the catheter. Thus, a delivery system must be capable of imparting a significant, yet controlled, force to retract the outer sheath and deploy the stent-graft. A need in the art still exists for an improved delivery system having a handle that consistently and reliably retracts the outer sheath thereof in order to deploy a prosthesis in a body lumen.

BRIEF SUMMARY OF THE INVENTION

Embodiments hereof are related to a delivery system for delivering a prosthesis, the delivery system including a housing, a sheath extending from within the housing, a clutching mechanism housed within the housing, and a cable. The clutching mechanism includes a one-way clutch that transmits a torque from an actuator to an inner shaft assembly when the actuator is rotated in a first direction and does not transmit a torque from the actuator to the inner shaft assembly when the actuator is rotated in a second opposing direction. The actuator is accessible from an exterior of the housing. The cable has a first end coupled to a proximal portion of the sheath and a second end coupled to the inner shaft assembly, and actuation of the actuator causes the actuator to rotate in the first direction, thereby causing the inner shaft assembly to wind up a portion of cable and retract the sheath.

According to another embodiment hereof, a delivery system for delivering a prosthesis includes a housing, a sheath extending from within the housing, an actuator accessible from an exterior of the housing, an inner shaft assembly disposed within the housing, a driving one-way clutch disposed between the actuator and a first portion of the inner shaft component of the inner shaft assembly, and a cable. The inner shaft assembly includes an inner shaft component, a transmitting one-way clutch, a storage drum concentrically disposed around or within the transmitting one-way clutch, and a bearing coupled to the housing and extending into or over the transmitting one-way clutch. The driving one-way clutch transmits a torque from the actuator to the inner shaft assembly when the actuator is rotated in a first direction and does not transmit a torque from the actuator to the inner shaft assembly when the actuator is rotated in a second opposing direction. The cable has a first end coupled to a proximal portion of the sheath and a second end coupled to the storage drum of the inner shaft assembly, and actuation of the actuator causes the actuator to rotate in the first direction, thereby causing the storage drum to wind up a portion of cable and retract the sheath. Release of the actuator causes the actuator to rotate in the second direction, and the bearing prevents the transmitting one-way clutch and storage drum from rotating in the second direction.

Embodiments hereof also relate to a delivery system for delivering a prosthesis including a handle having a housing, a sheath extending from within the housing, a self-expanding prosthesis disposed at a distal end of the delivery system, a clutching mechanism housed within the housing, and a cable. A distal end of the sheath constrains the prosthesis in a compressed configuration. The clutching mechanism includes an actuator, an inner shaft assembly, and a one-way clutch disposed between actuator and the inner shaft assembly, and the one-way clutch transmits a torque from the actuator to the inner shaft assembly when the actuator is rotated in a first direction and does not transmit a torque from the actuator to the inner shaft assembly when the actuator is rotated in a second opposing direction. The cable has a first end coupled to a proximal portion of the sheath and a second end coupled to the inner shaft assembly, and actuation of the actuator causes the actuator to rotate in the first direction, thereby causing the inner shaft assembly to wind up a portion of cable and retract the sheath to allow the prosthesis to expand to an deployed configuration.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1 is a side view of a delivery system according to an embodiment hereof, wherein an outer sheath of the delivery system surrounds and constrains a prosthesis in a compressed or delivery configuration.

FIG. 1A is a cross-sectional view taken along line A-A of FIG. 1.

FIG. 2 is a side view of the delivery system of FIG. 1, wherein the outer sheath has been retracted via a handle of the delivery system that includes a clutching mechanism in order to allow the prosthesis to self-expand to a deployed or expanded configuration.

FIG. 6 is a sectional view of a one-way clutch of the clutching mechanism of the handle of FIG. 1.

FIG. 6A is an enlarged view of a portion of the one-way clutch of FIG. 6.

FIG. 16 is a side view of the handle of FIG. 14 with the mechanical advantage of the actuator illustrated thereon.

DETAILED DESCRIPTION OF THE INVENTION

Figure 3:
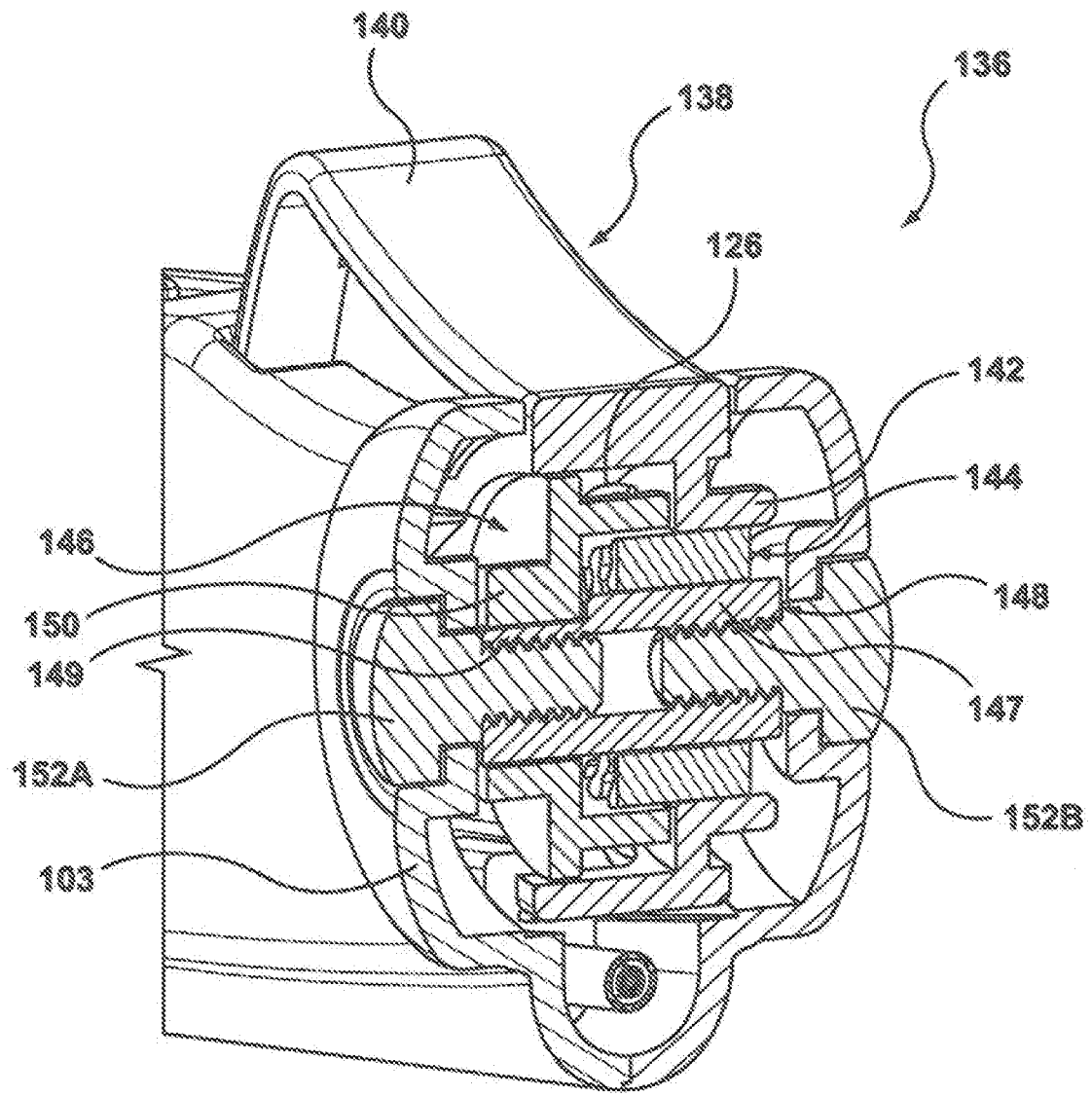
FIG. 3 is a perspective sectional view taken along line 3-3 of FIG. 1.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

Embodiments hereof are related to a delivery system having an improved handle that allows for operation of the delivery system with one hand while maintaining accuracy in delivery and deployment of a prosthesis in a body lumen. With reference to FIGS. 1, 1A, and 2, a delivery system 100 includes a handle 102, an inner shaft 112 having a proximal end 114 and a distal end 116, and an outer retractable sheath or cover 104 having a proximal end 106 and a distal end 108. Outer sheath 104 defines a lumen 110 and outer sheath 104 is slidingly disposed over inner shaft 112. Inner shaft 112 defines a lumen 118 such that delivery system 100 may be slidingly disposed and track over a guidewire 122. A tapered flexible nosecone or tip 120 may be coupled to distal end 116 of inner shaft 112. A self-expanding prosthesis 101 is mounted over inner shaft 112 at a distal portion thereof and outer sheath 104 surrounds and constrains prosthesis 101 in a compressed or delivery configuration as shown in the side view of FIG. 1 (prosthesis 101 shown only in the view of FIG. 2). In one embodiment, delivery system 100 may also include a retainer (not shown) which temporarily secures a proximal or first end of prosthesis 101 onto inner shaft 112 at distal end 116 thereof. For example, the retainer may include an end stent capture configuration as described in U.S. Patent Pub. 2009/0276027 to Glynn, which is hereby incorporated by reference herein in its entirety. The retainer operates to hold prosthesis 101 axially stationary with respect to handle 102 when outer sheath 104 is proximally retracted or withdrawn and prevents the proximal end of the prosthesis 101 adjacent distal end 116 of inner shaft 112 from radially expanding when sheath 104 is withdrawn.

As will be described in more detail herein, handle 102 includes a clutching mechanism 136 for proximally retracting outer sheath 104 in order to deploy or release prosthesis 101, thereby allowing prosthesis 101 to self-expand to a deployed or expanded configuration as shown in the side view of FIG. 2. Stated another way, a user operates handle 102 of delivery system 100 in order to withdraw or proximally retract outer sheath 104, thereby releasing prosthesis 101 at a desired location in a patient's body lumen. The deployed configuration of prosthesis 101 is merely exemplary, and it would be apparent to one of ordinary skill in the art that delivery system 100 may be utilized for delivering and deploying various types or configurations of self-expanding prostheses. A stopper 125 may be disposed over proximal end 114 of inner shaft 112. When deploying prosthesis 100, outer sheath 104 is proximally retracted until its proximal end 106 abuts against or contacts stopper 125 as shown in FIG. 2.

Figure 7:
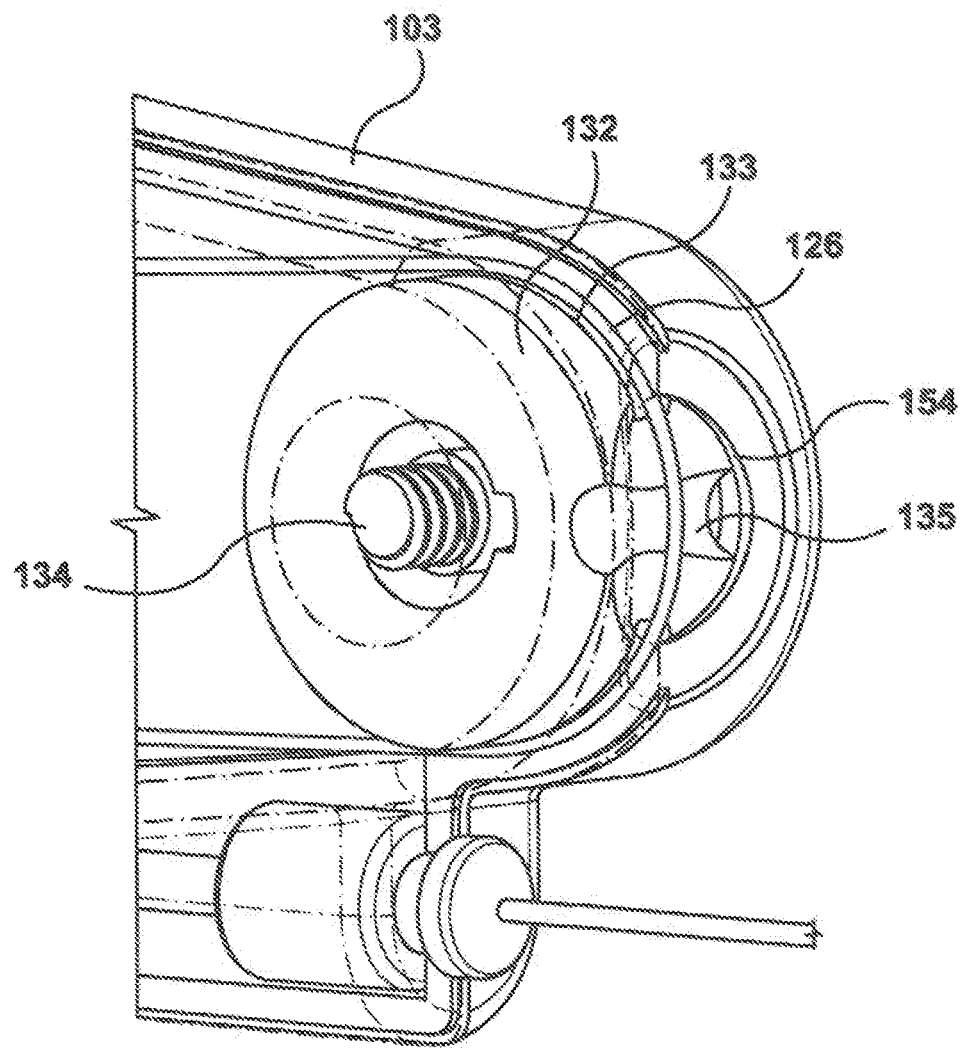
FIG. 7 is a perspective view of an access wheel of the handle of FIG. 1.

Handle 102 includes a cable or connector 126 having a first end coupled to proximal end 106 of outer sheath 104 via an anchor or coupler 124 and a second end fixed or attached to clutching mechanism 136. An intermediate portion of cable 126 is wound around an access wheel 132 disposed or housed within a proximal portion of handle 102. Access wheel 132 functions to allow a user to manually grasp and pull cable 126 to thereby retract outer sheath 104 independent from clutching mechanism 136. With additional reference to FIG. 7, access wheel 132 includes a circumferential groove or channel 133 formed on an outer surface thereof for receiving cable 126. A screw 134 extends through access wheel 132 to couple access wheel 132 to a housing 103 of handle 102. Housing 103 includes a window or opening 154 which provides access to cable 126 to a user if necessary. In addition, access wheel 132 may include a recess or cutout portion 135 which is located adjacent to opening 154 of housing 103. Recess 135 assists in providing access to cable 126 because a user may more easily grasp the portion of cable 126 which extends over recess 135.

Figure 5:
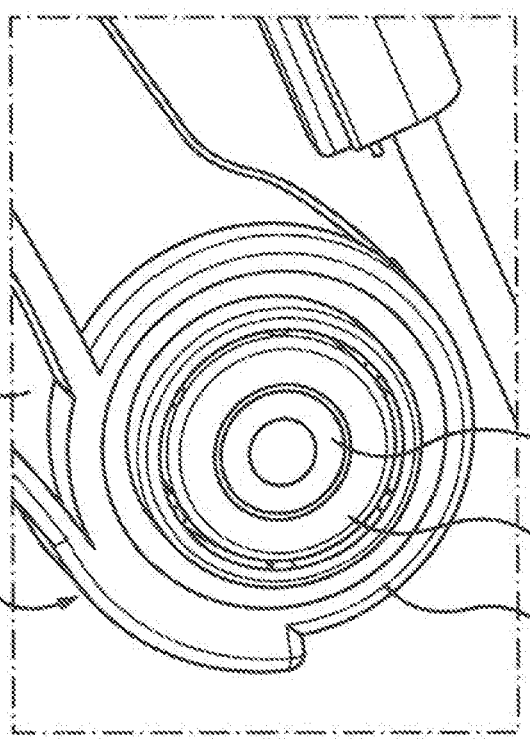
FIGS. 4-5 are perspective side views of the clutching mechanism of the handle of FIG. 1, wherein a housing of the handle has been removed for illustrative purposes.
Figure 4:
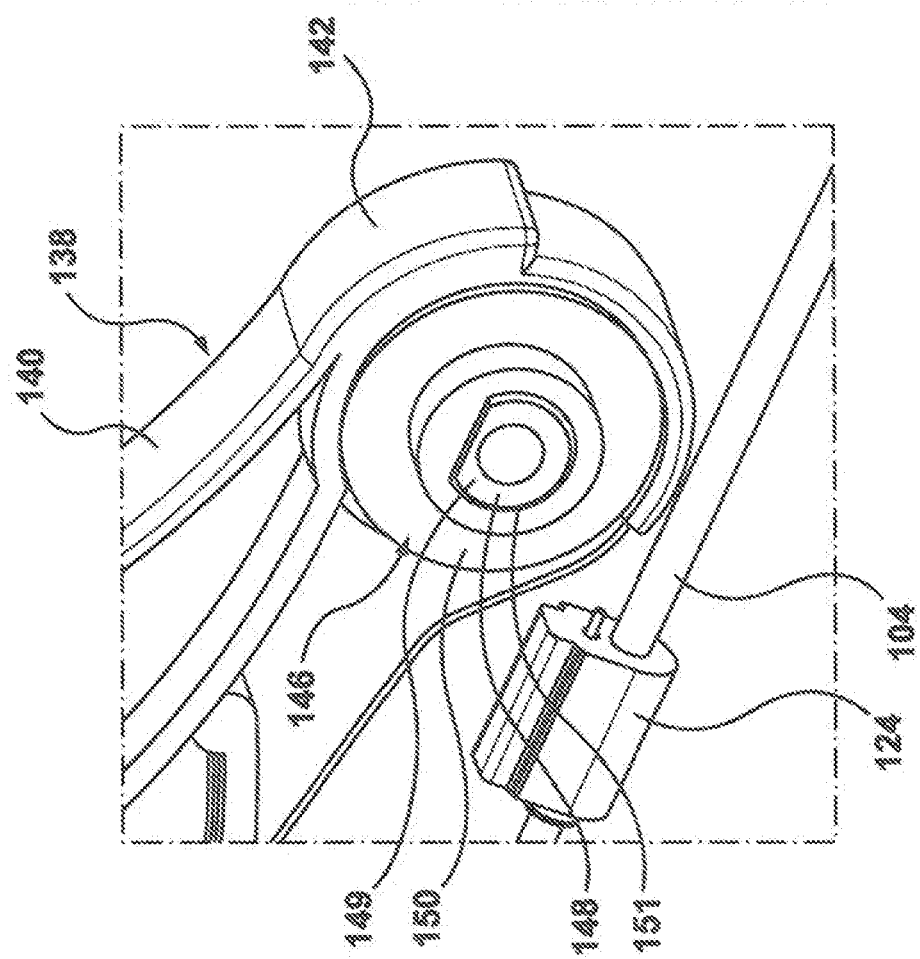

With additional reference to FIGS. 3, 4, and 5, clutching mechanism 136 will now be described in more detail. FIG. 3 is a cross-sectional view taken along line 3-3 of FIG. 1, and FIGS. 4-5 are perspective views of opposing sides of clutching mechanism 136 with housing 103 of handle 102 removed for illustrative purposes only. Clutching mechanism 136 includes an actuator or actuator assembly 138, an inner shaft assembly 146, and a one-way clutch 144 disposed between actuator 138 and the inner shaft assembly 146. More particularly, actuator assembly 138 includes a lever 140 which is mounted within housing 103 so as to be accessible and operable from an exterior of housing 103 and an outer wheel or shaft 142 which is coupled to or integrally formed with lever 140. One-way clutch 144 is press fit into outer shaft 142, thereby coupling the outer surface of one-way clutch 144 to outer shaft 142 such that an outer portion or component of one-way clutch 144 rotates or turns with outer shaft 142 as will be described in more detail herein. Inner shaft assembly 146 includes an inner shaft 148 having a first portion 147 disposed within one-way clutch 144 and a second portion 149 disposed within a storage drum 150. First portion 147 of inner shaft 148 is coupled to the inner surface of one-way clutch 144 via an interference or friction fit such that an inner portion or component of one-way clutch 144 rotates or turns with inner shaft 148 as will be described in more detail herein. Second portion 149 of inner shaft 148 is coupled to storage drum 150, which is concentrically disposed around the second portion 149 of inner shaft 148 and rotates or turns with inner shaft 148 as will be explained in more detail herein. One-way clutch 144 transmits a torque from actuator 138 to inner shaft assembly 146 when actuator 138 is rotated in a first direction, i.e., counter-clockwise, and does not transmit a torque from actuator 138 to inner shaft assembly 146 when actuator 138 is rotated in a second opposing direction, i.e., clockwise. Actuation of lever 140 causes actuator 138 to rotate in the first or counter-clockwise direction, and torque is transmitted to inner shaft assembly 146 via one-way clutch 144. As a result, inner shaft assembly 146 rotates in the first or counter-clockwise direction to wind up a portion of cable 126. Release of lever 140 causes actuator 138 to rotate in the second or clockwise direction, but one-way clutch 144 does not transmit torque to inner shaft assembly 146 in the clockwise direction so cable 126 does not unwind. As will be described in more detail below, repeated actuation or pumping of lever 140 thus results in winding an intermediate portion or length of cable 126 around inner shaft assembly 146 to proximally retract outer sheath 104 to the position shown in FIG. 2, thereby permitting prosthesis 101 to self-expand to the deployed configuration.

One-way clutch 144 is a uni-directional or single direction clutch bearing that is designed to transmit torque or a drive between a first component and a second component in one direction and allow free motion or freewheel in the opposite direction. As utilized herein, one-way clutch 144 is designed to transmit torque between actuator 138 and inner shaft assembly 146 in one direction and allow free motion or freewheel in the opposite direction. In an embodiment, as shown in FIGS. 6 and 6A, one-way clutch 144 may be a sprag clutch and include an annular outer support or component 156, an annular inner support or component 158, and a plurality of spring-loaded sprags 160 disposed between outer and inner supports 156, 158. The inner ends or surfaces of sprags 160 extend beyond inner support 158 and contact inner shaft 148 via an interference or friction fit therewith. When disposed within delivery system 100, outer support 156 of clutch 144 is coupled or attached to outer shaft 142 of actuator 138 via a press fit and thereby may be considered to move concurrently as an ensemble or subassembly therewith. Sprag clutches are commercially available from Outrage RC, LLC of Malden, Mass., as well as various other manufacturers. Sprags 160 are configured to become wedged or locked between outer and inner shafts 142, 148 when one of outer shaft 142 or inner shaft 148 is rotated in a particular direction, and thereby transmit or convey torque from the rotated support member to the other support member. In the configuration of FIGS. 6-6A, sprags 160 are configured to become wedged or locked between outer and inner shafts 142, 148 when outer shaft 142 is rotated in a counter-clockwise direction indicated by directional arrow 162A and/or when inner shaft 148 is rotated in a clockwise direction indicated by directional arrow 162B. As outer shaft 142 rotates counter-clockwise, sprags 160 pivot around their centerpoint and a larger height or dimension 168 of sprag 160 wedges sprag 160 between outer and inner shafts 142, 148, thereby locking or engaging the shafts together so that they turn or rotate as one. Stated another way, outer shaft 142 transmits or conveys torque to the inner shaft 148 when outer shaft 142 is rotated counter-clockwise because the wedging action provides or transfers a drive from outer shaft 142 to inner shaft 148. The same result occurs if inner shaft 148 is rotated clockwise, i.e., outer and inner shafts 142, 148 engage or lock together if inner shaft 148 is rotated clockwise. Conversely, when outer shaft 142 rotates clockwise as indicated by directional arrow 164A, sprags 160 pivot around their centerpoint and a smaller height or dimension 166 of sprag 160 disengages outer and inner shafts 142, 148 and allows outer shaft 142 and outer support 156 coupled thereto to spin over or freewheel relative to inner shaft 148. Stated another way, since sprags 160 are not wedged or locked between outer and inner shafts 142, 148, outer shaft 142 does not transmit or convey torque to the inner support when outer shaft 142 is rotated in a clockwise direction. The same result occurs if inner shaft 148 is rotated counter-clockwise as indicated by directional arrow 164B, i.e., inner shaft 148 spins or rotates freely within outer shaft 142 and outer support 156 coupled thereto when inner shaft 148 is rotated counter-clockwise. Two screws 152A, 152B couple clutching mechanism 136 to housing 103 of handle 102. Screws 152A, 152B extend into inner shaft 148 of inner shaft assembly 146, and an inner surface of inner shaft 148 includes threads which mate with threads on the outer surfaces of screws 152A, 152B such that inner shaft 148 may freely rotate or spin over screws 152A, 152B. In another embodiment hereof (not shown), one-way clutch 144 may be a roller-type clutch in which torque is positively transmitted by rollers that wedge against interior ramps or may be another type of uni-directional clutch known in the art.

Second portion or length 149 of inner shaft 149 is coupled to storage drum 150, as best shown in FIG. 4. More particularly, while first portion or length 147 of inner shaft 148 has a circular cross-section and is disposed within one-way clutch 144, second portion 149 of inner shaft 148 has a non-circular cross-section and is disposed within storage drum 150, which has an inner surface 151 which mates with the outer surface of second portion 149 of inner shaft 148. In an embodiment, the non-circular cross-section of second portion 149 of inner shaft 148 may be generally D-shaped. The D-shaped cross-section of second portion 149 may be formed by removing or cutting away a portion of inner shaft 148, although other manufacturing processes may also be used. When inner shaft 148 rotates or spins, storage drum 150 is effectively coupled thereto by the mating non-circular surfaces between the storage drum and second portion 149 of inner shaft 148. Accordingly, storage drum 150 turns or spins in the same direction as and with inner shaft 148 as one.

A second end of cable 126 is fixed or attached to storage drum 150. Thus, when inner shaft assembly 146 (inner shaft 148 and storage drum 150 coupled thereto) spins, cable 126 wraps or circles around storage drum 150. Each time lever 140 is pressed down or actuated, clutching mechanism 136 operates to transfer torque between actuator 138 and inner shaft assembly 146 and a relatively small length of cable 126 is wound around storage drum 150. As cable 126 is wound or circled around storage drum 150, outer sheath 104 moves proximally and axially with respect to housing 103 of housing 102. Repeated actuation or pumping of lever 140 results in continued winding of cable 126 and outer sheath 104 is gradually or incrementally withdrawn to release prosthesis 101. Stopper 125, mounted over proximal end 114 of inner shaft 112 as described above, limits the axial movement of outer sheath 104 with respect to housing 102. At the point in which outer shaft 104 abuts against stopper 125, prosthesis 101 is fully exposed or released from outer sheath 104 and permitted to self-expand to the deployed configuration as shown in FIG. 2. In an embodiment, between 15-35 cycles or pumps of lever 140 proximally retracts or withdraws proximal end 106 of outer sheath 104 to stopper 125 within handle 102 to fully deploy or release prosthesis 101. However, as will be understood by one of ordinary skill in the art, the number of lever cycles or pumps may vary depending upon the length of prosthesis 101, the distance that outer sheath 104 is required to travel in order to fully release the prosthesis, and how much of cable 126 is wound per pump. As also will be understood by one of ordinary skill in the art, the length of cable 126 wound with each pump may be varied by changing the size of drum 150 and/or how much drum 150 is rotated per pump.

Figure 8:
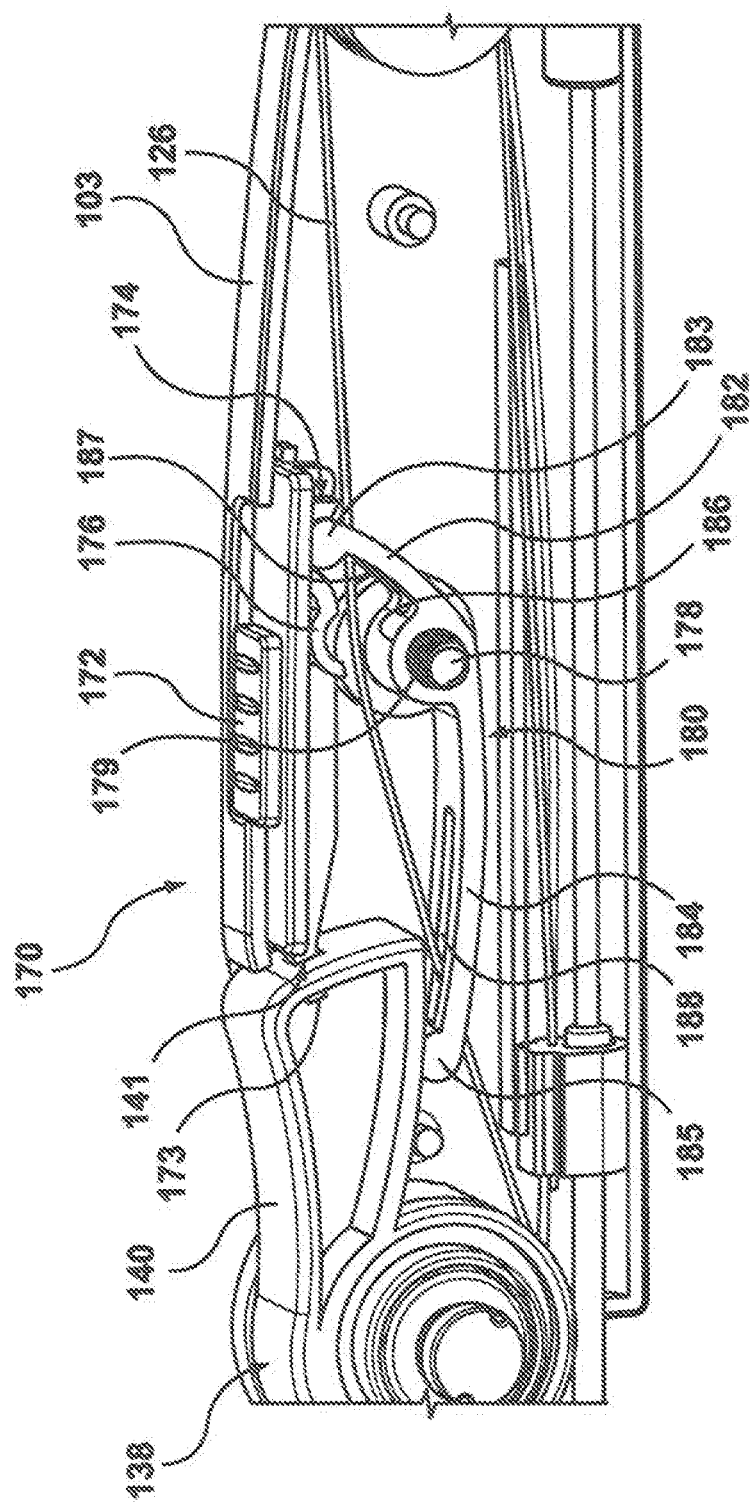
FIG. 8 is a side view of an actuator mechanism of the handle of FIG. 1 which may be used to transfer the delivery system from a storage or locked configuration to an operational or unlocked configuration, wherein the actuator is shown in the storage or locked configuration in FIG. 8.
Figure 9:
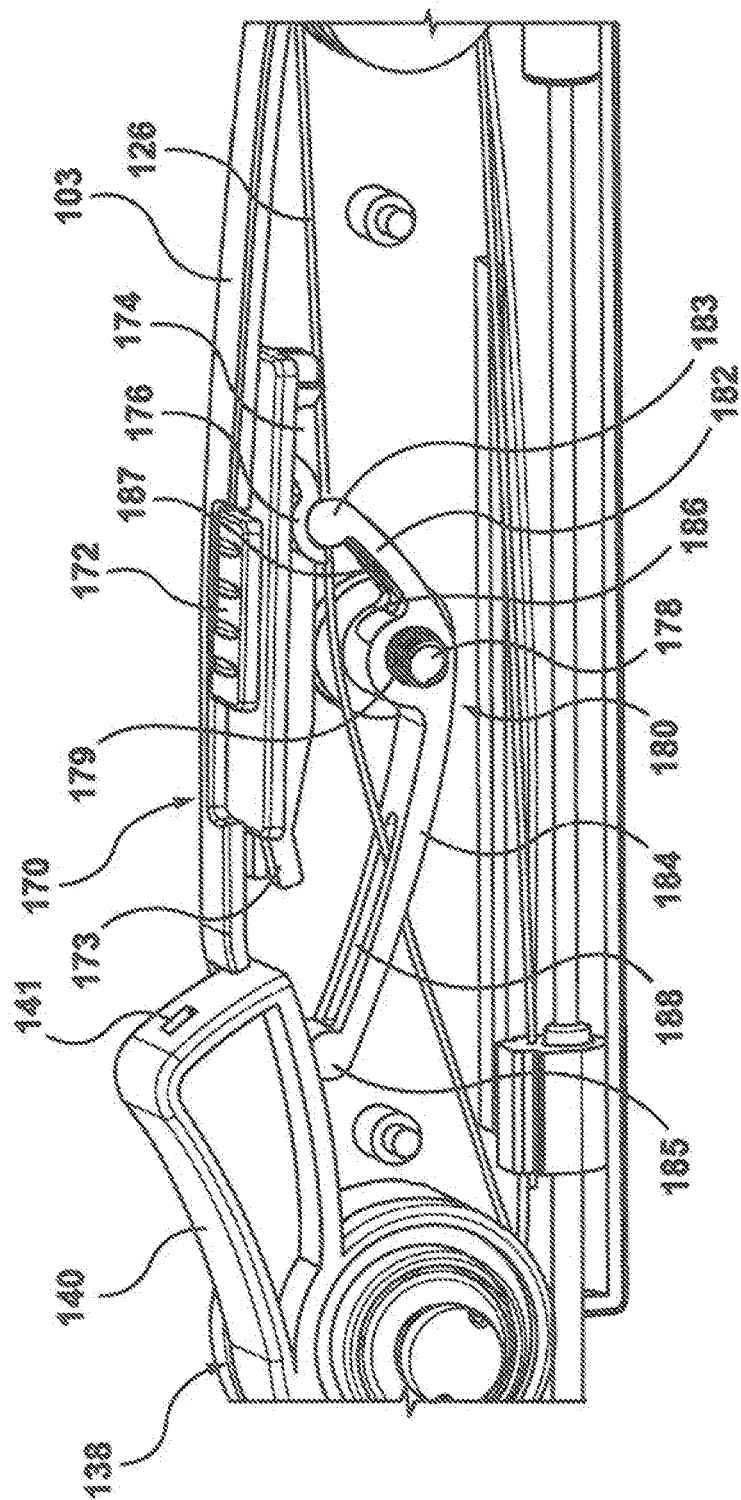
FIG. 9 is a side view of the actuator mechanism of FIG. 8, wherein the actuator is shown in the operational or unlocked configuration in FIG. 9.

Handle 102 may also include a second actuator mechanism 170 which may be used to transfer delivery system 100 from a storage or locked configuration, which is shown in FIG. 8, to an operational or unlocked configuration, which is shown in FIG. 9. FIGS. 8 and 9 are reversed from FIGS. 1 and 2 such that the proximal end of handle 102 is shown to the right and the distal end is shown to the left in FIGS. 8 and 9, while the proximal end of the handle 102 is shown to the left and the distal end is shown to the right in FIGS. 1 and 2. Second actuator mechanism 170 includes an actuator or slider 172 which includes a first or proximal socket or recess 174 and a second or distal socket or recess 176 on a surface thereof. Slider 172 is mounted within housing 103 so as to be accessible and operable from an exterior of housing 103, with sockets 174, 176 being positioned within housing 103. Second actuator mechanism 170 also includes a spring 180, which includes a first arm 182, a second arm 184, and a hinge 186 between arms 182, 184. Spring 180 is coupled to housing 103 via a screw 178, which extends though hinge 186 of spring 180. Screw 178 includes threads on an outer surface thereof for connecting two halves or portions of housing 103. Hinge 186 of spring 180 freely rotates or spins over an outer surface of a shoulder or raised portion 179 of screw 178. First and second arms 182, 184 include cylindrical elements or rods 183, 185, respectively, on the ends thereof and arms 182, 184 include openings or apertures 188, 187, respectively, to allow passage of cable 126 therethrough.

In the storage or locked configuration of FIG. 8, there is no tension on spring 180 and rod 183 of first arm 182 of spring 180 is disposed within proximal socket 174 of slider 172. Lever 140 is substantially flush with the outer surface of housing 103, and is thus not yet activated or ready for operation thereof. A distal end of slider 172 includes a tab or extension 173 that fits into an aperture or opening 141 of lever 140 to hold lever 140 in the storage or locked configuration. When it is desired to operate delivery system 100, slider 172 is advanced in a proximal direction such that tab 173 of slider 172 is withdrawn from aperture 141 in lever 140, thereby releasing lever 140 from slider 172 and to the operational or unlocked configuration of FIG. 9. Movement of slider 172 also forces rod 183 of first arm 182 of spring 180 into distal socket 176 of slider 172. Since distal socket 176 is positioned radially lower than proximal socket 174, spring 180 slightly rotates or turns in a clockwise direction as rod 183 transfers from proximal socket 174 to distal socket 176. When spring 180 rotates in a clockwise direction around hinge 186, rod 185 of second arm 184 pushes lever 140 upwards and radially away from the outer surface of housing 103 as shown in FIG. 9. Lever 140 is now activated and ready for operation thereof, and rod 183 of first arm 182 of spring 180 is locked within distal socket 176. When lever 140 is pumped or pressed down to retract outer sheath 104 as described above, second arm 184 of spring 180 bends radially downward but rod 183 of first arm 182 of spring 180 remains locked within distal socket 176. More particularly, without distal socket 176, spring 180 would rotate or turn in a counter-clockwise direction if second arm 184 of spring 180 is bent or pushed radially downward. Rod 183 of first arm 182 thus would move in a counter-clockwise direction, towards lever 140 which is located distal to slider 172. However, since rod 183 is secured or locked within distal recess 176, such counter-clockwise rotation of first arm 182 is prohibited. Thus, when lever 140 is pumped or pressed down, first arm 182 of spring 180 remains stationary while second arm 184 of spring 180 is sufficiently flexible to be bent down in conjunction with lever 140. When lever 140 is released, the tension within spring 180 and the sufficient resiliency of spring 180 causes second arm 184 to push lever 140 upwards and radially away from the outer surface of housing 103 back into the operational position of FIG. 9.

Figure 10:
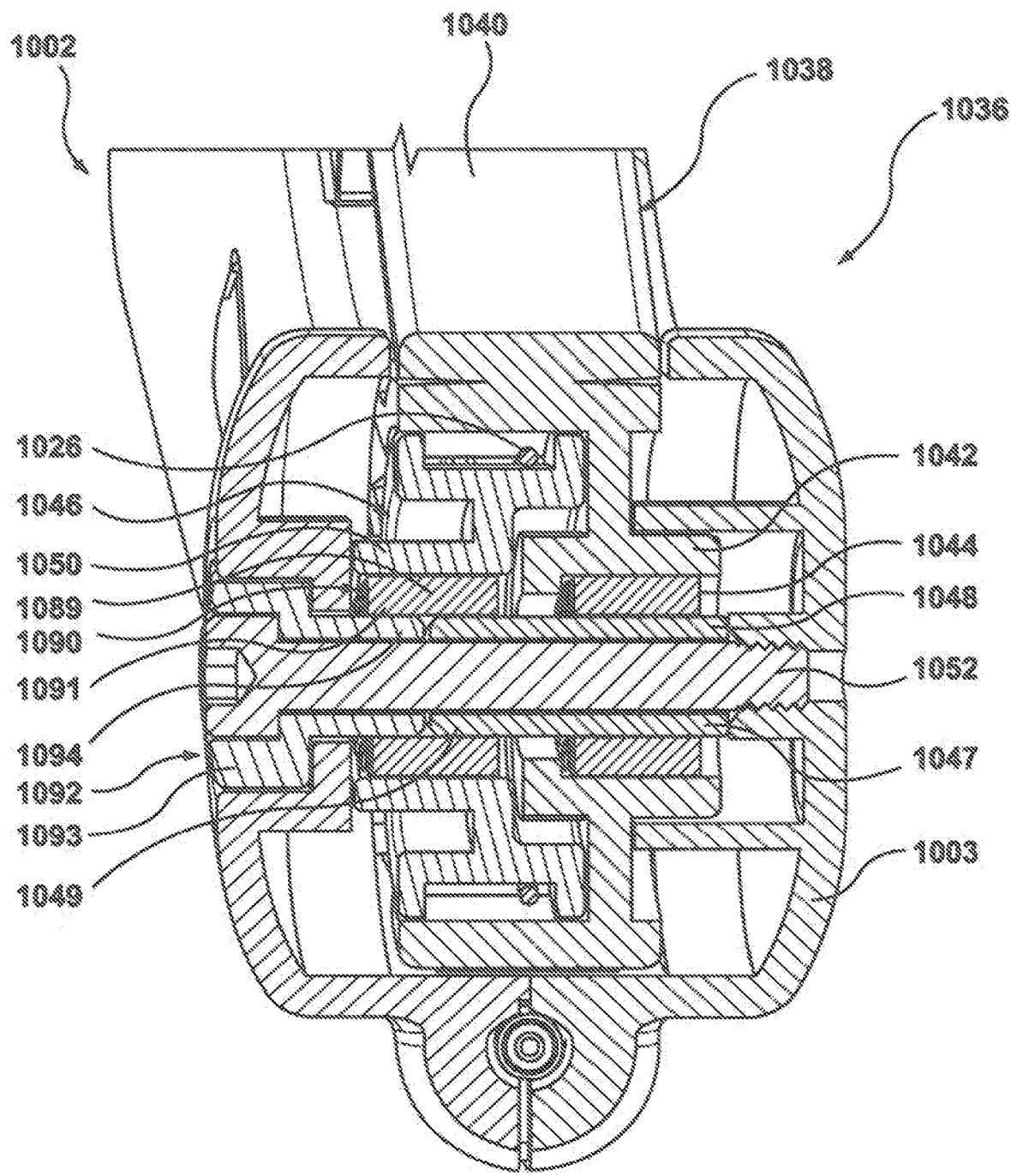
FIG. 10 is a perspective sectional view of a clutching mechanism according to an another embodiment hereof.

Another embodiment hereof is shown in FIG. 10, in which the clutching mechanism thereof includes additional components to further prevent any unwinding of the cable during operation thereof. During operation of the clutching mechanism and winding of the cable, there is considerable tension developed as the inner shaft assembly reels in the cable that retracts the outer shaft. When the actuator or lever is released, the cable in some instances may tend to slightly recoil and undesirably cause the storage drum to rotate, thereby unreeling or unwinding cable 126 from the inner shaft assembly. Accordingly, clutching mechanism 1036 of FIG. 10 includes a second or transmitting one-way clutch 1090 and a stationary bushing or bearing 1092 extending through a portion of the second one-way clutch 1090 in order to prevent such undesired unwinding of a cable 1026. Stationary bearing 1092 is coupled to housing 1003 of handle 1002 and thus cannot rotate. More particularly, stationary bearing 1092 includes a first portion or segment 1093 and a second portion or segment 1094. While second portion 1094 of stationary bearing 1092 has a circular cross-section and is disposed within transmitting clutch 1090, first portion 1093 of stationary bearing 1092 has a non-circular cross-section and is disposed through an opening of housing 1003, which has an inner surface which mates with the outer surface of first portion 1093 of stationary bearing 1092. In an embodiment, the non-circular cross-section of first portion 1093 of stationary bearing 1092 may be generally D-shaped. Stationary bearing 1092 is effectively coupled to housing 1003 by the mating non-circular surfaces between the stationary bearing and the housing.

Similar to clutching mechanism 136, clutching mechanism 1036 includes an actuator or actuator assembly 1038, an inner shaft assembly 1046, and a first or driving one-way clutch 1044 disposed between actuator 1038 and the inner shaft assembly 1046. Actuator or actuator assembly 1038 includes a lever 1040 which is mounted within housing 1003 so as to be accessible and operable from an exterior of housing 1003 and an outer wheel or shaft 1042 which is coupled to or integrally formed with lever 1040. One-way clutch 1044 is press fit into outer shaft 1042, and thereby an outer surface or component of clutch 1044 is coupled to outer shaft 1042. A first portion 1047 of inner shaft 1048 is disposed through and coupled to an inner surface or component of driving one-way clutch 1044. Similar to the previous embodiment, driving one-way clutch 1044 transmits a torque from actuator 1038 to inner shaft assembly 1046 when actuator 1038 is rotated counter-clockwise, and does not transmit a torque from actuator 1038 to inner shaft assembly 1046 when actuator 1038 is rotated clockwise. Stated another way, driving clutch 1044 drives or rotates inner shaft assembly 1046 in the counter-clockwise direction and freewheels or idles around inner shaft assembly in the clockwise direction.

Inner shaft assembly 1046 includes inner shaft 1048, transmitting one-way clutch 1090 concentrically disposed around a second portion 1049 of inner shaft 1048 and second portion 1094 of stationary bearing 1092, and a storage drum 1050 concentrically disposed around transmitting one-way clutch 1090. Transmitting one-way clutch 1090 is press fit or embedded into storage drum 1050, thereby coupling an outer surface or support component of transmitting one-way clutch 1090 to storage drum 1050. A first portion or length 1089 of transmitting clutch 1090 is disposed over second portion 1049 of inner shaft 1048, and a second portion or length 1091 of transmitting clutch 1090 is disposed over second portion 1094 of stationary bearing 1092. Transmitting one-way clutch 1090 has an opposing or opposite configuration or orientation than driving one-way clutch 1044, meaning that transmitting one-way clutch 1090 is configured to transmit a torque from storage drum 1050 to inner shaft 1048 when storage drum 1050 is rotated clockwise, and does not transmit a torque from storage drum 1050 to inner shaft 1048 when storage drum 1050 is rotated counter-clockwise. Stated another way, with respect to rotation of storage drum 1050, transmitting one-way clutch 1090 drives or rotates inner shaft 1048 in the clockwise direction and freewheels or idles around inner shaft 1048 in the counter-clockwise direction. As explained above, inner shaft 1048 transmits or does not transmit a torque to storage drum 1050 through rotation in the opposite direction of storage drum 1050. More particularly, transmitting one-way clutch 1090 is configured to transmit a torque from inner shaft 1048 to storage drum 1050 when inner shaft 1048 is rotated counter-clockwise, and does not transmit a torque from inner shaft 1048 to storage drum 1050 when inner shaft 1048 is rotated clockwise. Stated another way, with respect to rotation of inner shaft 1048, transmitting one-way clutch 1090 drives or rotates storage drum 1050 in the counter-clockwise direction and freewheels or idles within storage drum 1050 in the clockwise direction.

Figure 11:
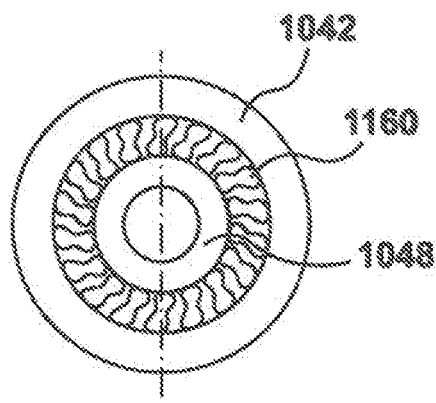
FIG. 11 is a sectional view of a driving one-way clutch of the clutching mechanism of the handle of FIG. 10.
Figure 11A:
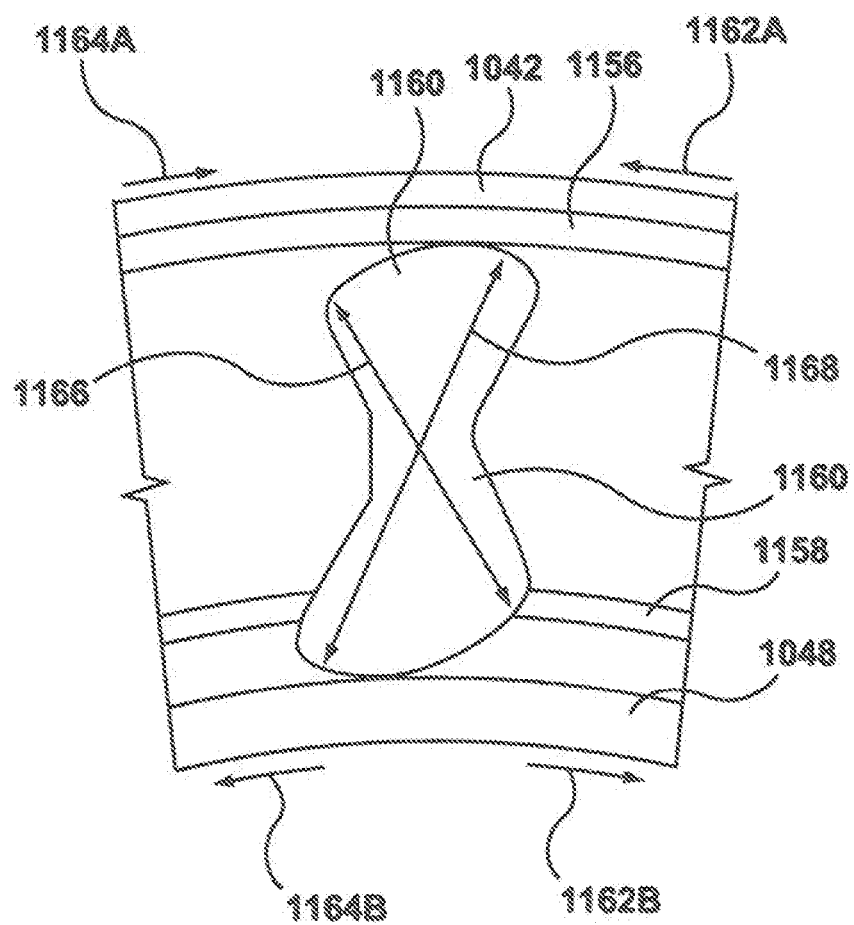
FIG. 11A is an enlarged view of a portion of the driving one-way clutch of FIG. 11.
Figure 12:
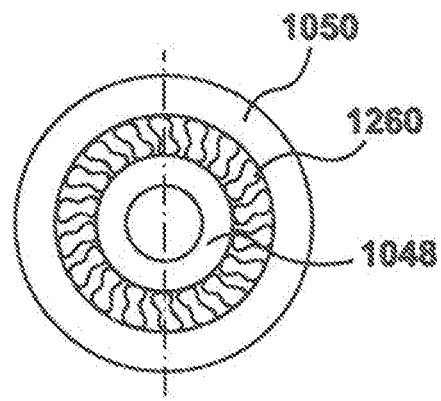
FIG. 12 is a sectional view of a transmitting one-way clutch of the clutching mechanism of the handle of FIG. 10.
Figure 12A:
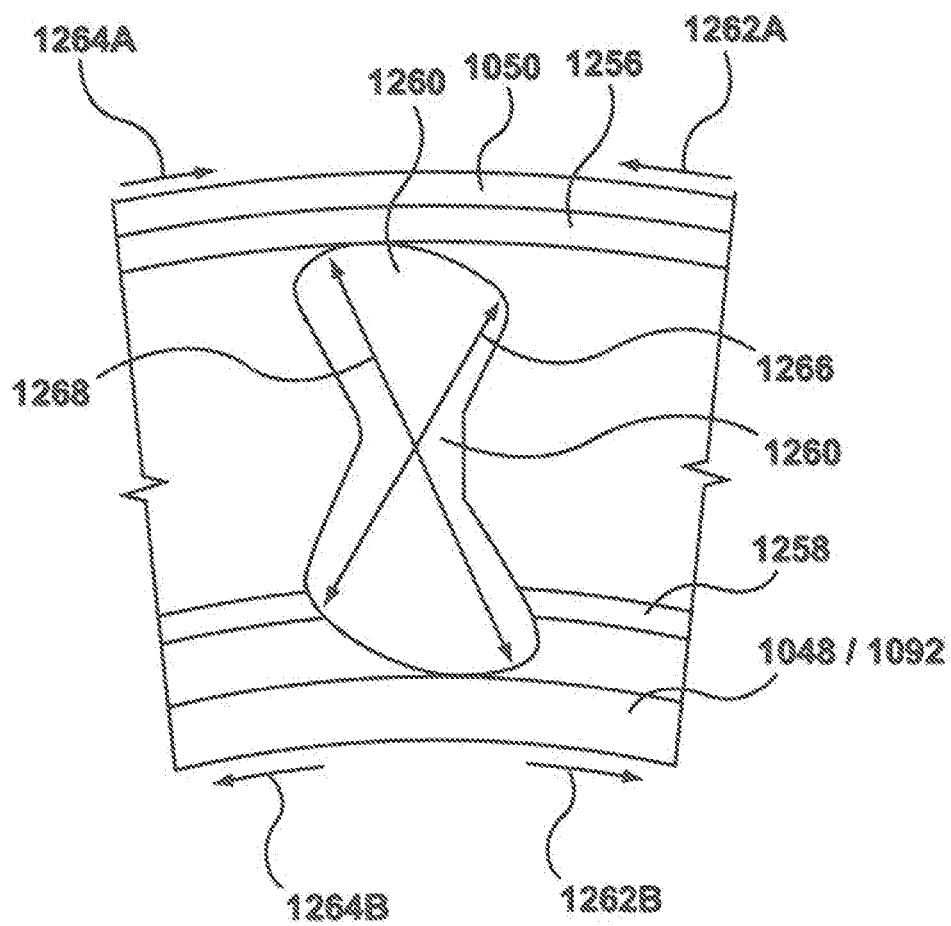
FIG. 12A is an enlarged view of a portion of the transmitting one-way clutch of FIG. 12.

More particularly, the opposing orientations or configurations of clutches 1044 and 1090 may be seen through a comparison of FIGS. 11 and 12. Driving clutch 1044 includes an annular outer support 1156, an annular inner support 1158, and a plurality of spring-loaded sprags 1160 and is shown in FIGS. 11 and 11A, while transmitting clutch 1090 includes an annular outer support 1256, an annular inner support 1258, and a plurality of spring-loaded sprags 1260 and is shown in FIGS. 12 and 12A. Similar to sprags 160 of one-way clutch 144, sprags 1160 of driving clutch 1044 are configured to become wedged or locked between outer and inner shafts 1042, 1048 when outer shaft 1042 is rotated counter-clockwise as indicated by directional arrow 1162A and/or inner shaft 1048 is rotated in clockwise as indicated by directional arrow 1162B. As outer shaft 1042 rotates counter-clockwise, sprags 1160 pivot around their centerpoint and a larger height or dimension 1168 of sprag 1160 wedges sprag 1160 between outer and inner shafts 1042, 1048, thereby locking or engaging the shafts together so that they turn or rotate as one. When outer shaft 1042 rotates clockwise as indicated by directional arrow 1164A, sprags 1160 pivot around their centerpoint and a smaller height or dimension 1166 of sprag 1160 allows outer shaft 1042 to spin over or freewheel relative to inner shaft 1048. The same result occurs if inner shaft 1048 is rotated counter-clockwise as indicated by directional arrow 1164A, i.e., inner shaft 1042 spins or rotates freely within outer shaft 1048 and outer support 1156 when inner shaft 1048 is rotated in a counter-clockwise direction.

Conversely, sprags 1260 of transmitting clutch 1090 are configured to become wedged or locked between storage drum 1050 and inner shaft 1048/stationary bearing 1092 when storage drum 1050 is rotated clockwise as indicated by directional arrow 1264A and/or inner shaft 1048 is rotated counter-clockwise as indicated by directional arrow 1264B. In FIG. 12A, since first portion length 1089 of transmitting clutch 1090 is disposed over second portion 1049 of inner shaft 1048 and second portion 1091 of transmitting clutch 1090 is disposed over second portion 1094 of stationary bearing 1092, the inner member is labeled as both inner shaft 1048 and stationary bearing 1092. As storage drum 1050 rotates clockwise, sprags 1260 pivot around their centerpoint and a larger height or dimension 1268 of sprags 1160 wedges sprags 1260 between storage drum 1050 and inner shaft 1048/stationary bearing 1092, thereby locking or engaging the components together. The same result occurs if inner shaft 1048 is rotated counter-clockwise, i.e., storage drum 1050 and inner shaft 1048 engage or lock together if inner shaft 1048 is rotated counter-clockwise. When storage drum 1050 rotates counter-clockwise as indicated by directional arrow 1262A, sprags 1260 pivot around their centerpoint and a smaller height or dimension 1266 of sprags 1260 allows storage drum 1050 to spin or rotate freely over or freewheel relative to inner shaft 1048/stationary bearing 1050. The same result occurs if inner shaft 1048 is rotated clockwise as indicated by directional arrow 1262B, i.e., inner shaft 1048 spins or rotates freely within storage drum 1050 when inner shaft 1048 is rotated in a clockwise direction.

During operation, i.e., when lever 1040 is pressed down, actuation of lever 1040 causes actuator 1038 to rotate counter-clockwise and torque is transmitted to inner shaft 1048 via driving one-way clutch 1044. When inner shaft 1048 rotates counter-clockwise, i.e., as shown by the directional arrow 1264B of FIG. 12A, storage drum 1050 and inner shaft 1048 engage or lock together via sprags 1260 and thus transmitting one-way clutch 1090 drives storage drum 1050 counter-clockwise such that inner shaft assembly 1046 winds up a portion of cable 1026. Stated another way, when lever 1040 is pressed, inner shaft 1048 is driven counter-clockwise and transmitting one-way clutch 1090 transmits the counter-clockwise torque from inner shaft 1048 to storage drum 1050 to wind up cable 1026. During this torque transmittal step, sprags 1260 are wedged between second portion 1049 of inner shaft 1048 and storage drum 1050 so that sprags 1260 transfers the counter-clockwise torque from the inner shaft to the storage drum. However, as storage drum 1050 rotates counter-clockwise, sprags 1260 of second portion or segment 1091 of transmitting one-way clutch 1090 do not engage or wedge with respect to stationary bearing 1092 and thus storage drum 1050 and outer support 1256 coupled thereto is freewheeling in the counter-clockwise direction over stationary bearing 1092.

As previously stated, there is considerable tension building as cable 1026 is wound around storage drum 1050 and thus it is desirable to prevent undesired unwinding of the cable when lever 1040 is released. When storage drum 1050 tries to unwind and rotate clockwise due to recoil of cable 1026, such rotation of storage drum 1050 is prevented due to transmitting one-way clutch 1090 and stationary bearing 1092. More particularly, when storage drum 1050 tries to unwind and rotate clockwise, transmitting one-way clutch 1090 engages stationary bearing 1092 to rotate in the clockwise direction as well. However, stationary bearing 1092 cannot rotate since it is fixed to housing 1003. Thus, stationary bearing 1092 prevents transmitting one-way clutch 1090 and storage drum 1050 from rotating in the clockwise direction. Because stationary bearing 1092 extends through second portion 1091 of transmitting one-way clutch 1090, stationary bearing 1092 prevents or retards the transfer of torque in the clockwise direction and therefore prevents motion of transmitting one-way clutch 1090 and storage drum 1050 coupled thereto in the clockwise direction. Accordingly, unwinding or unreeling of cable 1026 is prevented.

Figure 13:
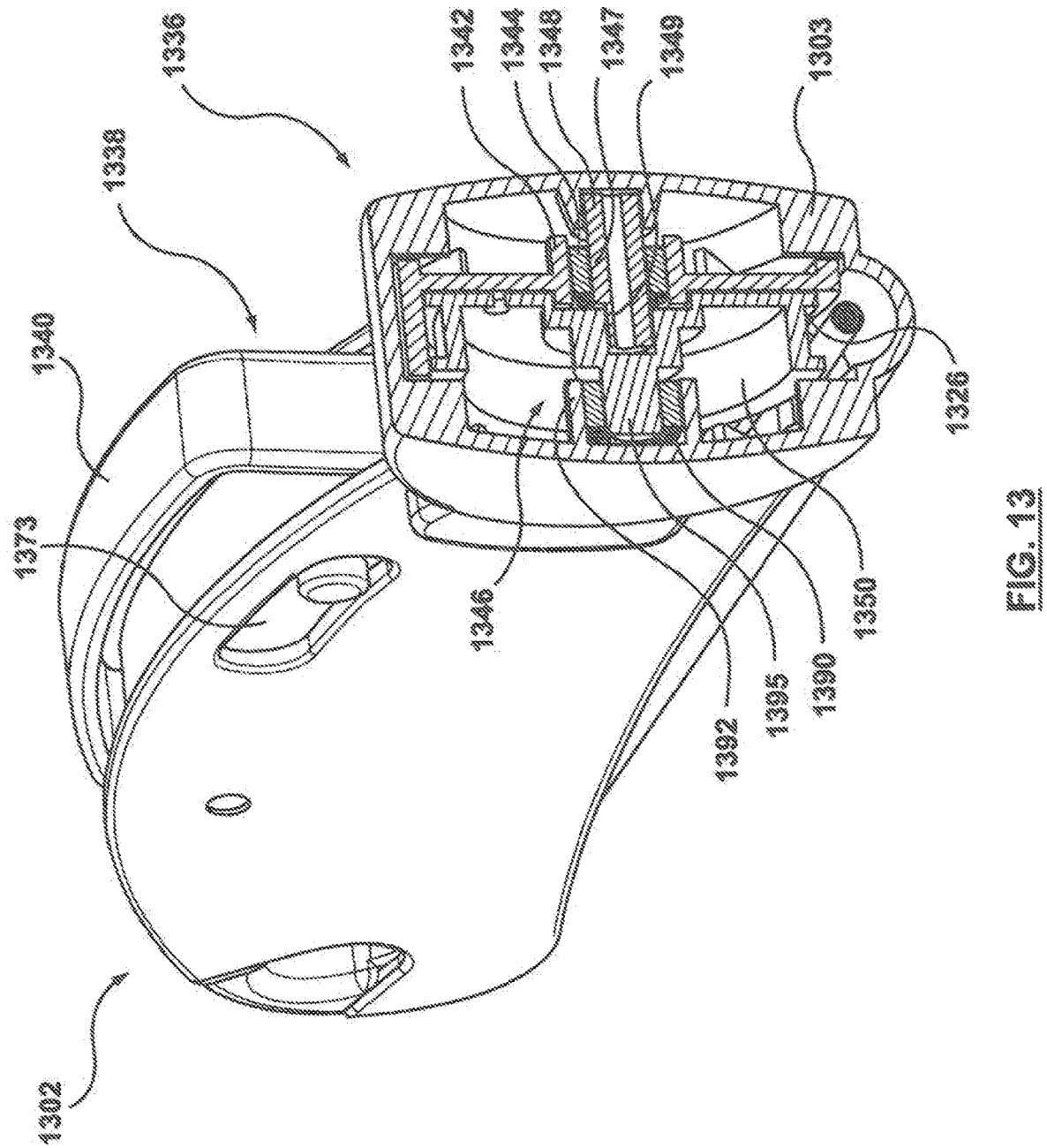
FIG. 13 is a sectional view of a one-way clutch of a clutching mechanism according to another embodiment hereof.

Another embodiment hereof is shown in FIG. 13, in which the clutching mechanism thereof has a different configuration to further prevent any unwinding of the cable during operation thereof. Similar to the clutching mechanism of FIG. 10, clutching mechanism 1336 includes a second or transmitting one-way clutch 1390 and a stationary bushing or bearing 1392 in order to prevent such undesired unwinding of a cable 1326. Stationary bearing 1392 is coupled to housing 1303 of handle 1302 and thus cannot rotate. However, in FIG. 10, the stationary bearing extends through a portion of the transmitting one-way clutch, while in FIG. 13 stationary bearing 1392 extends over a portion of transmitting one-way clutch 1390.

Similar to previous embodiments, clutching mechanism 1336 includes an actuator or actuator assembly 1338, an inner shaft assembly 1346, and a first or driving one-way clutch 1344 disposed between actuator 1338 and the inner shaft assembly 1346. Actuator or actuator assembly 1338 includes a lever 1340 which is mounted within housing 1303 so as to be accessible and operable from an exterior of housing 1303 and an outer wheel or shaft 1342 which is coupled to or integrally formed with lever 1340. One-way clutch 1344 is press fit into outer shaft 1342, and thereby an outer surface or component of clutch 1344 is coupled to outer shaft 1342. A first portion 1347 of inner shaft 1348 is disposed through and coupled to driving one-way clutch 1344. Similar to the previous embodiment, driving one-way clutch 1344 transmits a torque from actuator 1338 to inner shaft assembly 1346 when actuator 1338 is rotated counter-clockwise, and does not transmit a torque from actuator 1338 to inner shaft assembly 1346 when actuator 1338 is rotated clockwise. Stated another way, driving clutch 1344 drives or rotates inner shaft assembly 1346 in the counter-clockwise direction and freewheels or idles around inner shaft assembly in the clockwise direction.

Inner shaft assembly 1346 includes a second portion or length 1349 of inner shaft 1348, a storage drum 1350 concentrically disposed around second portion 1349 of inner shaft 1348, and transmitting one-way clutch 1390 concentrically disposed around an extension 1395 of storage drum 1350. Second portion or length 1349 of inner shaft 1348 has a non-circular cross-section and is disposed within and coupled to storage drum 1350 as described above with respect to second portion 149 of inner shaft 148 and storage drum 150. Accordingly, storage drum 1350 turns or spins in the same direction as and with inner shaft 1348 as one. Transmitting one-way clutch 1390 is press fit or embedded into stationary bearing 1392, thereby coupling an outer surface or support component of transmitting one-way clutch 1390 thereto. Transmitting one-way clutch 1390 has the same configuration or orientation as driving one-way clutch 1344. Thus, when storage drum 1350 is rotated or driven counter-clockwise, extension 1395 of storage drum 1350 freewheels or idles within transmitting one-way clutch 1390. However, when storage drum tries to rotate in a clockwise direction, extension 1395 of storage drum 1350 engages stationary bearing 1392 via transmitting one-way clutch 1390 and thus rotation is prevented.

More particularly, winding of cable 1326 occurs similar to winding of cable 126 described above. During operation, i.e., when lever 1340 is pressed down, actuation of lever 1340 causes actuator 1338 to rotate counter-clockwise and torque is transmitted to inner shaft 1348 and storage drum 1350 coupled thereto via driving one-way clutch 1344. As a result, inner shaft 1348 and storage drum 1350 coupled thereto rotate counter-clockwise to wind up a portion of cable 1326. During this torque transmittal step, since storage drum 1350 is driven counter-clockwise, extension 1395 of storage drum 1350 freewheels or idles within transmitting one-way clutch 1390.

As previously stated, there is considerable tension building as cable 1326 is wound around storage drum 1350 and thus it is desirable to prevent undesired unwinding of the cable when lever 1340 is released. When storage drum 1350 tries to unwind and rotate clockwise due to recoil of cable 1326, such rotation of storage drum 1350 is prevented due to transmitting one-way clutch 1390 and stationary bearing 1392. More particularly, when storage drum 1350 tries to unwind and rotate clockwise, extension 1395 of storage drum 1350 engages transmitting one-way clutch 1390 and stationary bearing 1392 to rotate in the clockwise direction as well. However, stationary bearing 1392 cannot rotate since it is fixed to housing 1303. Thus, stationary bearing 1392 prevents transmitting one-way clutch 1390 and storage drum 1350 from rotating in the clockwise direction. Accordingly, unwinding or unreeling of cable 1326 is prevented.

The embodiment of FIG. 13 includes lever 1340, which has a different configuration than lever 140, 1040 previously described. In the embodiments of FIGS. 1 and 10, each pump or cycle of lever 140, 1040 moves the storage drum through approximately twenty degrees of rotation such that between 15-35 cycles or pumps of lever 140 proximally retracts the outer sheath to fully deploy or release prosthesis 101. In the embodiment of FIG. 13, each pump or cycle of lever 1340 moves the storage drum through approximately forty-five degrees of rotation, thereby reducing the number of cycles or pumps required to fully retract the outer sheath. Accordingly, in an embodiment hereof, between 5-20 cycles or pumps of lever 1340 proximally retracts the outer sheath to fully deploy or release prosthesis 101. As will be understood by one of ordinary skill in the art, the levers described herein are interchangeable and any lever embodiment described herein may be used in combination with any clutching mechanism described herein. Lever 1340 is a cantilever handle.

Figure 14:
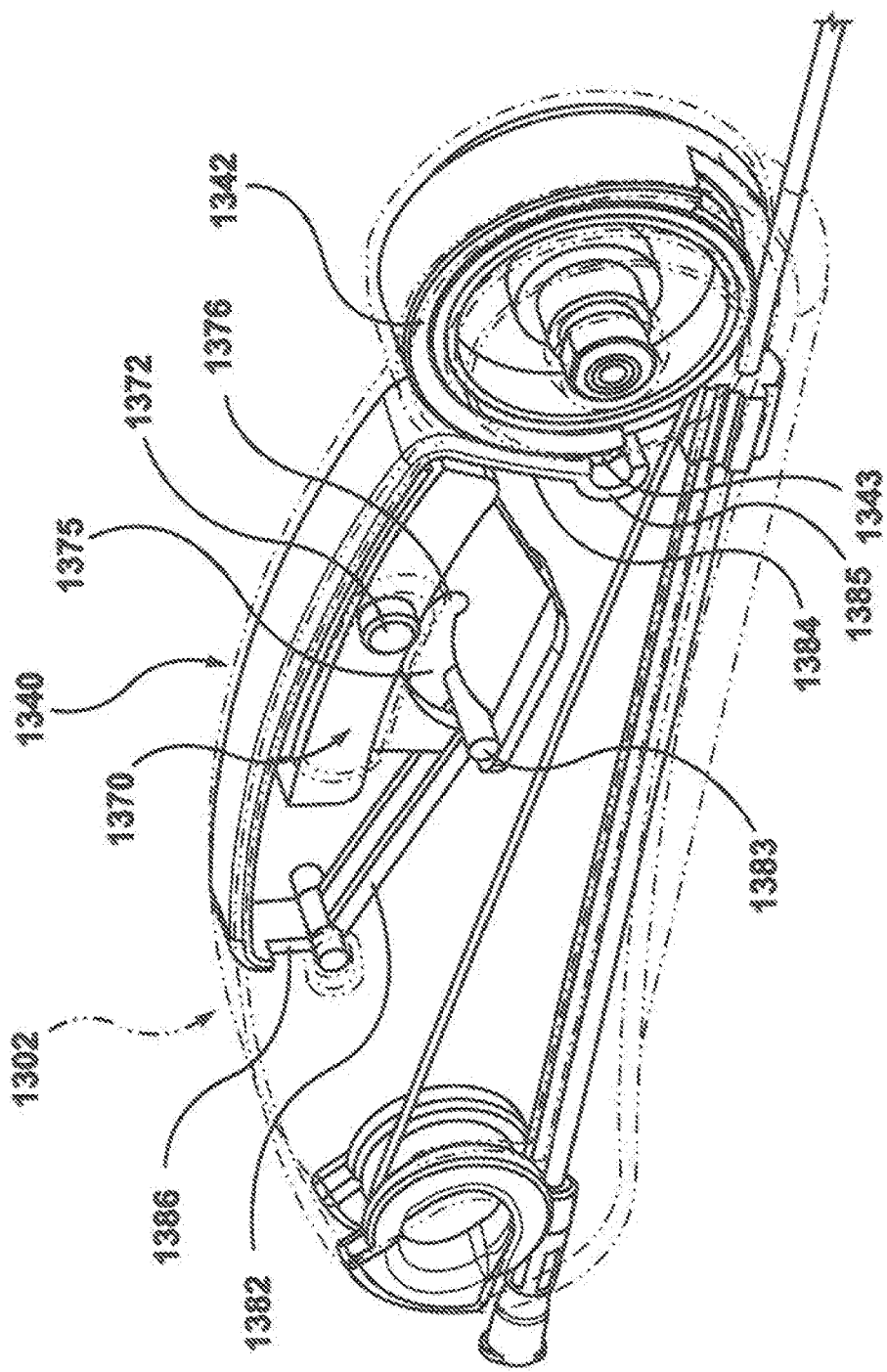
FIG. 14 is a perspective view of a handle according to an embodiment hereof, wherein an actuator thereof is shown in a storage or locked configuration.
Figure 15:
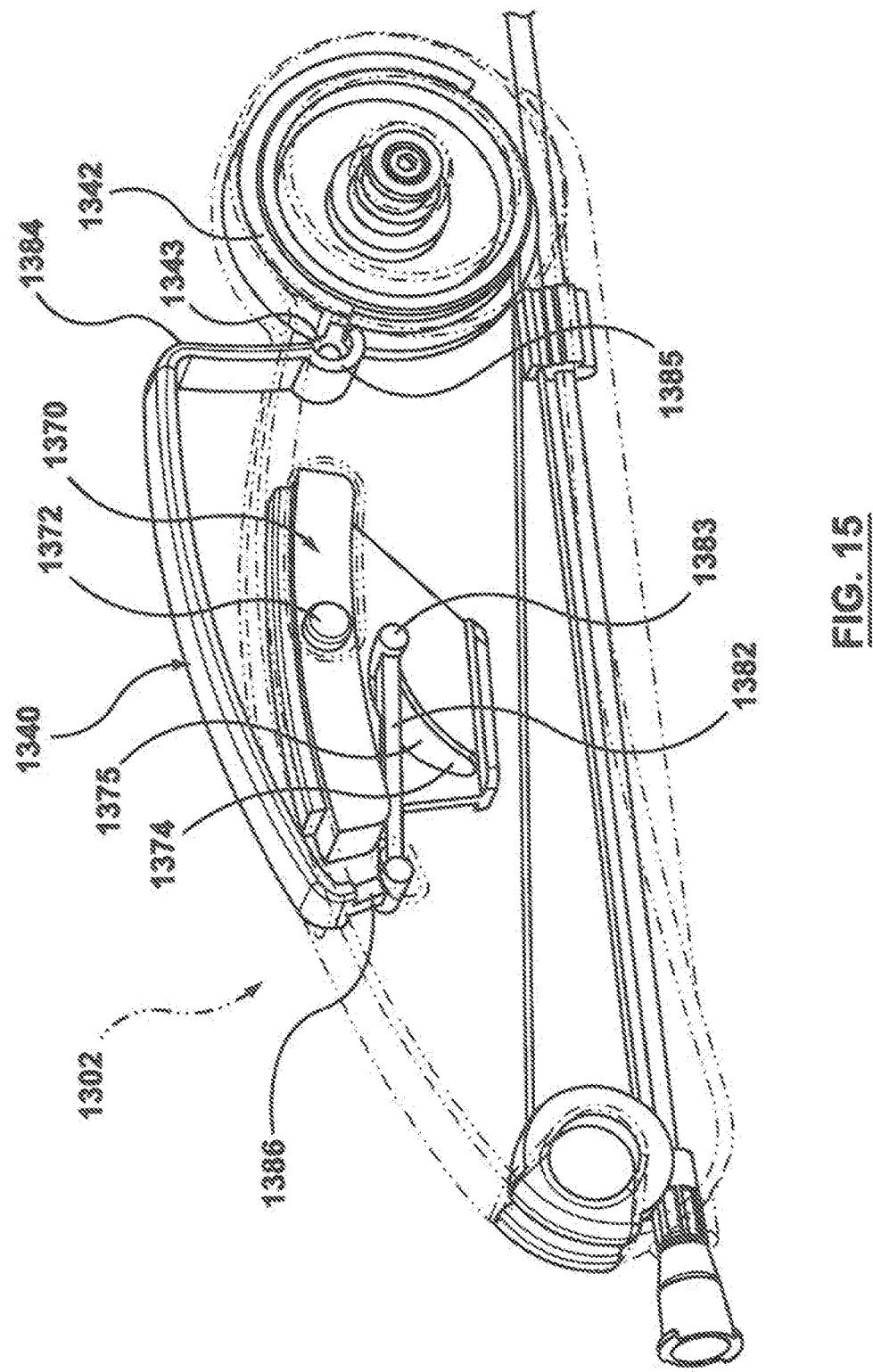
FIG. 15 is a side view of the handle of FIG. 14, wherein the actuator thereof is shown in an operational or unlocked configuration.

More particularly, the operation and structure of lever 1340 is described with reference to FIGS. 14-16. FIG. 14 illustrates lever 1340 in a storage or locked configuration, while FIG. 15 illustrates lever 1340 in an operational or unlocked configuration. A second actuator mechanism 1370 is utilized for shift or transfer lever 1340 from the storage configuration into the operational configuration. Second actuator mechanism 1370 is mounted within housing 1303 and includes an extension tab or button 1372 which extends from within housing 1303 through opening or slot 1373 (shown in FIG. 13) so as to be accessible and operable from an exterior of housing 103. Actuator mechanism 1370 includes a curved slot or opening 1375 formed there through, the curved slot having a first end or socket 1374 and a second opposing end or socket 1376. Lever 1340 may be considered a spring and includes a first arm 1382, a second arm 1384, and a hinge 1386 between arms 1382, 1384. First arm 1382 has a cylindrical element or rod 1383 at its end which is configured to slide within slot 1375 of actuator mechanism 1370, and second arm 1384 has a clip 1385 at its end which is configured to engage and couple to outer shaft 1342, for example, through a rod or tab 1343 extending from outer shaft 1342. As would be understood by those skilled in the art, other connections are possible. For example, and not by way of limitation, clip 1385 and rod 1343 may be reversed such that a rod at the end of second arm 1384 fits into a clip extending from outer shaft 1342, as shown schematically in FIG. 17.

In the storage or locked configuration of FIG. 14, there is no tension on lever 1340 and rod 1383 of first arm 1382 is disposed within socket 1374 of slot 1375 of actuating mechanism 1370. Lever 1340 is substantially flush with the outer surface of housing 1303, and is thus not yet activated or ready for operation thereof. When it is desired to operate lever 1340, tab 1372 is advanced in a proximal direction such that actuating mechanism 1370 is moved proximally. As actuating mechanism 1370 moves proximally, rod 1383 of first arm 1382 slides or moves into socket 1376 of slot 1375. Since slot 1375 is curved and socket 1376 is positioned radially higher than proximal end 1374, lever 1340 slightly rotates or turns in a counter-clockwise direction as rod 1383 transfers from socket 1374 to socket 1376. When lever 1340 rotates in a counter-clockwise direction around hinge 1386, clip 1385 of second arm 1384 is pulled upwards and radially away from the outer surface of housing 1303 as shown in FIG. 15. Lever 1340 is now activated and ready for operation thereof, and rod 1383 of first arm 1382 is locked within socket 1376 of slot 1375 of slider 1372. When lever 1340 is pumped or pressed down to retract the outer sheath, second arm 1384 of lever 1340 is pushed downward, thereby pushing rod 1343 of outer shaft 1342 to rotate outer shaft 1342, as shown in FIG. 16. Rod 1383 of first arm 1372 remains locked within socket 1376 of slot 1375 when lever 1340 is pressed down. When lever 1340 is released, the tension within hinge 1386 and the sufficient resiliency thereof causes hinge 1386 to move back to its original position of FIG. 15, thereby pulling second arm 1384 upward to its original configuration of FIG. 15 in which it extends upwards and radially away from the outer surface of housing 1303. Further, because outer shaft 1342 rotates freely in the clockwise direction, as described above, outer shaft 1342 does not provide significant resistance to lever 1340 returning to the position of FIG. 15.

The mechanical advantage of lever 1340 is illustrated in the side view of FIG. 16. When lever 1340 is pressed down or pumped, second arm 1384 of lever 1340 moves or rotates around hinge 1386 a first angle $\theta_1$. In an embodiment hereof, first angle $\theta_1$ is between 10-20 degrees. In response to movement of second arm 1384, storage drum 1350 moves or rotates a second angle $\theta_2$. In an embodiment hereof, second angle $\theta_2$ is between 40-50 degrees. The mechanical advantage of lever 1340 thus minimizes the number of pumps or cycles required to fully retract the outer sheath.

Figure 18:
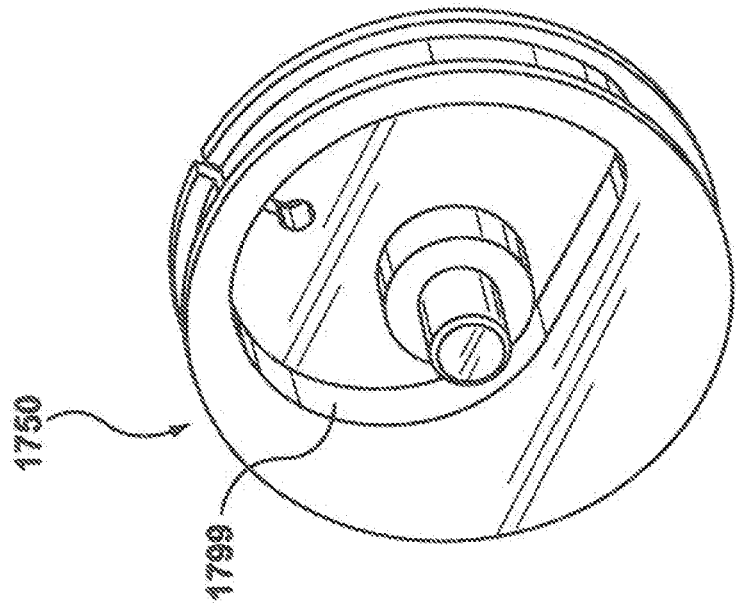
FIG. 18 is a perspective view of the storage drum of FIG. 17, wherein the storage drum is removed from the handle for illustrative purposes only.
Figure 17:
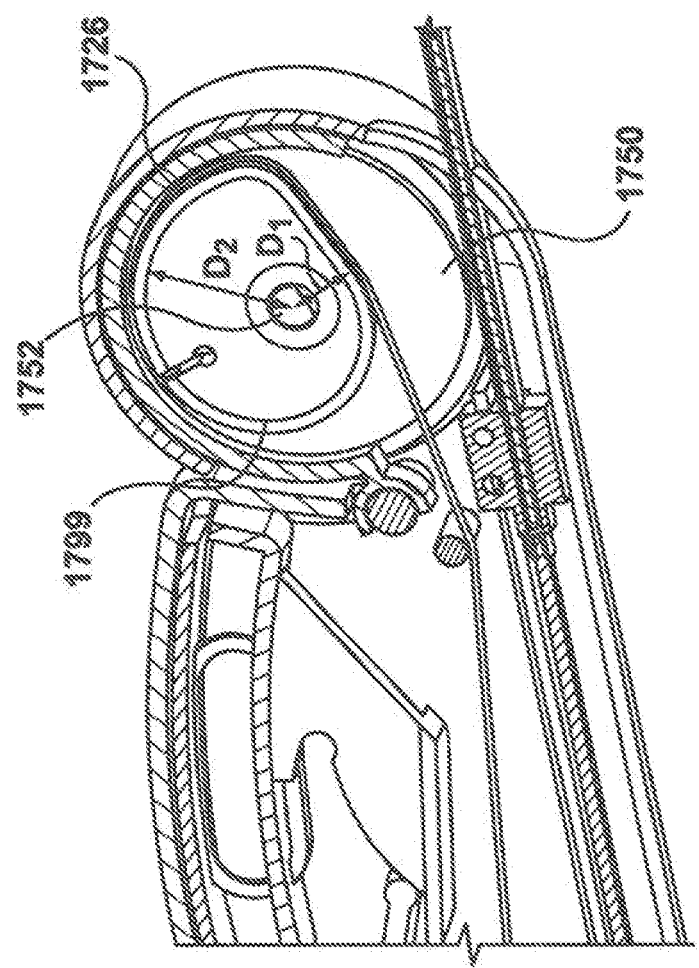
FIG. 17 is a perspective view of a portion of a handle according to another embodiment hereof, wherein the handle includes a storage drum having a non-circular track formed thereon for gathering a cable at a variable rate.

FIGS. 17-18 illustrate a storage drum 1750 that may be utilized with any embodiment described herein. Storage drum 1750 moves or rotates at a constant speed but gathers or winds the cable at a variable increasing rate. More particularly, storage drum 1750 includes a non-circular track 1799 formed therein and a screw 1752 extends through storage drum 1750. Screw 1752 is off-center relative to track 1799 due to track 1799 not having the same central axis as storage drum 1750. For sake of this description, track 1799 may be considered to have two integral portions. A first portion of track 1799 extends a relatively shorter distance or length from screw 1752, illustrated by example by a distance $D_1$, while a second portion of track 1799 extends a relatively longer distance or length from screw 1752, illustrated by example by a distance $D_2$. A first end of a cable 1726 is coupled to storage drum 1750 as shown in FIG. 17. As storage drum 1750 rotates counter-clockwise to wind up cable 1726, storage drum 1750 moves or rotates a constant angle $\theta_2$ as shown and described with respect to FIG. 16. When the cable is wound or guided around the first portion of track 1799, which extends a relatively shorter distance from screw 1752, a relatively shorter length or amount of cable 1726 is wound around storage drum 1750. Conversely, when the cable is wound or guided around the second portion of track 1799, which extends a relatively longer distance from screw 1752, a relatively longer length or amount of cable 1726 is wound around storage drum 1750. Thus, in operation, relatively shorter lengths of cable 1726 are wound up with a first or initial series of pumps or cycles of the lever and relatively longer lengths of cable 1726 are wound up with a second or final series of pumps or cycles of the lever. By gathering the cable at a variable increasing rate, storage drum 1750 allows the user to initially retract the outer sheath at a slower rate when placement of the stent-graft is not yet permanent and/or may be subject to change or adjustment. However, after retraction of the outer sheath has progressed to a certain point or stage in which placement of the stent-graft is permanent and/or not subject to change or adjustment, the outer sheath is retracted at a faster rate to minimize the number of required pumps or cycles.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. For example, it should be noted that although the clutching mechanisms of handles 102, 1002 are shown as being mounted within distal portions of housings 103, 1003, respectively, with the levers thereof extending in a proximal direction, this configuration is exemplary and is not meant to be limiting. As would be understood by those of ordinary skill in the art, the clutching mechanisms of handles 102, 1002 can be positioned in a variety of configurations with respect to housings 103, 1003, respectively. For example, the clutching mechanisms of handles 102, 1002 could be mounted near a midpoint of housings 103, 1003, respectively, or could be mounted within proximal portions of housings 103, 1003. In addition, although levers 140, 1040 are shown disposed at distal ends of housings 103, 1003, respectively, and extending in a proximal direction, the levers could alternatively be disposed at proximal ends of their respective housings and extend in a distal direction. In such a configuration, pressing the levers down for actuation thereof would rotate the actuators in a clockwise configuration. Accordingly, the one-way clutches of the clutching mechanisms would be configured to transfer a torque to the inner shaft assemblies when rotated clockwise and would be configured to freewheel over the inner shaft assemblies when released and rotated counter-clockwise. It will also be understood that each feature of each embodiment discussed herein, and of each reference cited herein, can be used in combination with the features of any other embodiment. All patents and publications discussed herein are incorporated by reference herein in their entirety.

The following detailed description is merely exemplary in nature and is not intended to limit the invention or the application and uses of the invention. Although the description of the invention is in the context of treatment of blood vessels such as the coronary, carotid and renal arteries, the invention may also be used in any other body passageways where it is deemed useful. Furthermore, there is no intention to be bound by any expressed or implied theory presented in the preceding technical field, background, brief summary or the following detailed description.

What is claimed is:

1. A delivery system for delivering a prosthesis, the delivery system comprising:
    a housing;
    a sheath extending from within the housing;
    a clutching mechanism housed within the housing, the clutching mechanism including a one-way clutch that transmits a torque from an actuator to an inner shaft assembly when the actuator is rotated in a first direction and does not transmit a torque from the actuator to the inner shaft assembly when the actuator is rotated in a second opposing direction, wherein the actuator is accessible from an exterior of the housing;
    a cable having a first end coupled to a proximal portion of the sheath and a second end coupled to a storage drum of the inner shaft assembly, wherein actuation of the actuator causes the actuator to rotate in the first direction, thereby causing the inner shaft assembly to wind up a portion of cable around the storage drum and retract the sheath; and
    an access wheel within the housing, wherein an intermediate portion of the cable is wound around the access wheel, and wherein the housing includes a window formed through the housing, the window being located adjacent to the access wheel.

2. The delivery system of claim 1, wherein release of the actuator causes the actuator to rotate in the second direction, thereby causing the one-way clutch to freely spin over the inner shaft assembly.

3. The delivery system of claim 1, wherein the actuator includes a lever and an outer shaft component concentrically disposed over the one-way clutch.

4. The delivery system of claim 1, wherein the inner shaft assembly includes an inner shaft component, the storage drum being concentrically disposed around a first portion of the inner shaft component and the one-way clutch being concentrically disposed around a second portion of the inner shaft component.

5. The delivery system of claim 4, wherein the storage drum is coupled to the inner shaft component via mating non-circular surfaces between the storage drum and the first portion of the inner shaft component.

6. The delivery system of claim 4, wherein the storage drum includes a non-circular track formed thereon for gathering the cable at a variable rate.

7. The delivery system of claim 4, wherein the actuator includes a lever that rotates a first angle and causes the storage drum to rotate a second angle, wherein the second angle is greater than the first angle.

8. The delivery system of claim 7, wherein the first angle is between 10 and 20 degrees and the second angle is between 40 and 50 degrees.

9. The delivery system of claim 1, wherein the storage drum is disposed at a first end of the housing and the access wheel is disposed at a second end of the housing.

10. A delivery system for delivering a prosthesis, the delivery system comprising:
    a handle having a housing;
    a sheath extending from within the housing;
    a clutching mechanism housed within the housing, the clutching mechanism including an actuator, an inner shaft assembly, and a one-way clutch disposed between actuator and the inner shaft assembly, wherein the one-way clutch transmits a torque from the actuator to the inner shaft assembly when the actuator is rotated in a first direction and does not transmit a torque from the actuator to the inner shaft assembly when the actuator is rotated in a second opposing direction;
    a cable having a first end coupled to a proximal portion of the sheath and a second end coupled to the inner shaft assembly, wherein actuation of the actuator causes the actuator to rotate in the first direction, thereby causing the inner shaft assembly to wind up a portion of cable and retract the sheath to allow the prosthesis to expand to an deployed configuration; and a locking mechanism configured to transfer the actuator between a storage configuration in which the actuator is substantially flush with an outer surface of the housing and an operational configuration in which the actuator is spaced outwardly from the outer surface of the housing.

11. The delivery system of claim 10, wherein release of the actuator causes the actuator to rotate in the second direction, thereby causing the one-way clutch to freely spin over the inner shaft assembly.

12. The delivery system of claim 11, wherein the inner shaft assembly includes an inner shaft component, a transmitting one-way clutch, a storage drum concentrically disposed around or within the transmitting one-way clutch, and a bearing coupled to the housing and extending into or over the transmitting one-way clutch, wherein the bearing prevents the transmitting one-way clutch and storage drum from rotating in the second direction.

13. The delivery system of claim 10, wherein the locking mechanism includes a slider with a first recess and a second recess and a spring including a first arm, a second arm, and a hinge between the first and second arms, wherein the second arm of the spring is coupled to the actuator, wherein in the storage configuration a first rod at a first end of the first arm opposite the hinge is disposed in the first recess of the slider, and wherein in the operational configuration the slider is moved such that the first rod at the first end of the first arm is disposed in the second recess of the slider.

14. The delivery system of claim 13, wherein the slider further includes a tab that fits into an aperture of the actuator to hold actuator in the storage configuration.

15. The delivery system of claim 10,
wherein the actuator includes a lever having a first arm, a second arm, and a hinge between the first arm and the second arm,
wherein the locking mechanism includes an extension tab which extends from within the housing through a slot so as to be accessible and operable from an exterior of the housing,
wherein the locking mechanism includes a curved slot formed therethrough having a first socket and a second socket opposite the first socket,
wherein a first rod of the first arm opposite the hinge is configured to slide within the slot of the locking mechanism,
wherein a clip at a first end of the second arm opposite the hinge is coupled to an outer shaft disposed around the clutching mechanism,
wherein in the storage configuration the extension tab is in a first location such that the first rod of the first arm is disposed within the first socket of the slot and the lever is substantially flush with the outer surface of housing, and
wherein in the operational configuration, the extension tab is moved to a second location such that the first rod of the first arm is disposed in the second socket and the lever is spaced apart from the outer surface of the housing.

16. A delivery system for delivering a prosthesis, the delivery system comprising:
a housing;
a sheath extending from within the housing;
a clutching mechanism housed within the housing, the clutching mechanism including,
an actuator accessible from an exterior of the housing,
an outer shaft coupled to the actuator such that rotation of the actuator in a first direction causes rotation of the outer shaft in the first direction and rotation of the actuator in a second direction causes rotation of the outer shaft in the second direction opposite the first direction,
an inner shaft disposed concentrically within the outer shaft, the inner shaft having a first portion and a second portion,
a one-way clutch disposed concentrically between the first portion of the inner shaft and the outer shaft, wherein the one-way clutch transmits a torque from the outer shaft to the first portion of the inner shaft when the actuator is rotated in the first direction and does not transmit a torque from the actuator to the first portion of the inner shaft when the actuator is rotated in the second opposing direction,
a storage drum disposed concentrically around the second portion of the inner shaft, wherein the storage drum is coupled to the second portion of the inner shaft such that rotation of the first portion of the inner shaft causes rotation of the second portion of the inner shaft and rotation of the second portion of the inner shaft causes rotation of the storage drum, wherein the storage drum is coupled to the second portion of the inner shaft via mating non-circular surfaces between the storage drum and the second portion of the inner shaft; and
a cable having a first end coupled to a proximal portion of the sheath and a second end coupled to the storage drum, wherein actuation of the actuator causes the actuator to rotate in the first direction, thereby causing the storage drum to wind up a portion of cable and retract the sheath, and wherein release of the actuator causes the outer shaft to rotate in the second direction but does not cause the storage drum to rotate.

17. The delivery system of claim 16, wherein the storage drum includes a non-circular track formed thereon for gathering the cable at a variable rate.

18. The delivery system of claim 16, further comprising an access wheel within the housing, wherein an intermediate portion of the cable is wound around the access wheel, and wherein the housing includes a window formed through the housing, the window being located adjacent to the access wheel.

19. The delivery system of claim 16, wherein the actuator includes a lever that rotates a first angle and causes the storage drum to rotate a second angle, wherein the second angle is greater than the first angle.

20. The delivery system of claim 19, wherein the first angle is between 10 and 20 degrees and the second angle is between 40 and 50 degrees.

* * * * *